United States Patent
Yang et al.

(10) Patent No.: US 10,851,346 B2
(45) Date of Patent: Dec. 1, 2020

(54) MTOR/STAT3 SIGNAL INHIBITOR-TREATED MESENCHYMAL STEM CELL HAVING IMMUNOMODULATORY ACTIVITY, AND CELL THERAPY COMPOSITION COMPRISING SAME, FOR PREVENTING OR TREATING IMMUNE DISORDERS

(71) Applicant: THE CATHOLIC UNIVERSITY OF KOREA INDUSTRY-ACADEMIC COOPERATION FOUNDATION, Seoul (KR)

(72) Inventors: Chul Woo Yang, Seoul (KR); Mi-La Cho, Seoul (KR); Sung-Hwan Park, Seoul (KR); Eun Kyung Kim, Seoul (KR); Byung Ha Chung, Seoul (KR); Kyoung-Woon Kim, Seoul (KR); Seon-Yeong Lee, Gyeonggi-do (KR); Sung-Hee Lee, Seoul (KR); Eun Ji Yang, Seoul (KR); Jeong-hee Jeong, Seoul (KR); Min Jung Park, Incheon (KR); Seok-Jung Kim, Seoul (KR); Eun-Jung Lee, Gyeonggi-do (KR); Su-Jin Moon, Seoul (KR)

(73) Assignee: THE CATHOLIC UNIVERSITY OF KOREA INDUSTRY—ACADEMIC COOPERATION FOUNDATION, Seoul (KR)

( * ) Notice: Subject to any disclaimer, the term of this patent is extended or adjusted under 35 U.S.C. 154(b) by 275 days.

(21) Appl. No.: 14/912,391

(22) PCT Filed: Aug. 14, 2014

(86) PCT No.: PCT/KR2014/007583
§ 371 (c)(1),
(2) Date: Feb. 16, 2016

(87) PCT Pub. No.: WO2015/023147
PCT Pub. Date: Feb. 19, 2015

(65) Prior Publication Data
US 2016/0289640 A1 Oct. 6, 2016

(30) Foreign Application Priority Data
Aug. 16, 2013 (KR) .......... 10-2013-0097218
Aug. 12, 2014 (KR) .......... 10-2014-0104575

(51) Int. Cl.
*C12N 5/0775* (2010.01)
*C07K 14/715* (2006.01)
*A61K 38/17* (2006.01)
*A61K 35/28* (2015.01)

(52) U.S. Cl.
CPC ............ *C12N 5/0667* (2013.01); *A61K 35/28* (2013.01); *A61K 38/177* (2013.01); *C07K 14/7158* (2013.01); *C12N 5/0665* (2013.01); *C12N 2501/04* (2013.01)

(58) Field of Classification Search
None
See application file for complete search history.

(56) References Cited

U.S. PATENT DOCUMENTS

| 8,455,245 B2 * | 6/2013 | Frank | C12N 5/0668 435/325 |
| 2002/0085996 A1 | 7/2002 | McIntosh et al. | |
| 2007/0020230 A1 * | 1/2007 | Kaps | A61K 38/195 424/85.1 |

(Continued)

FOREIGN PATENT DOCUMENTS

WO    WO 9951275 A2    10/1999

OTHER PUBLICATIONS

Wynn et al., A small proportion of mesenchymal stem cells strongly expresses functionally active CXCR4 receptor capable of promoting migration to bone marrow, Blood, vol. 104, No. 9, 2004, pp. 2643-2645.*
Body Weight Information for BALB/cJ, JAX Mice Strain—BALB/cJ; retrieved from the Internet, May 22, 2017: www.jax.org/jax-mice-and-services/strain-data-sheet-pages/body-weight-chart-000651.*
Warner et al., Review of prescribed treatment for children with asthma in 1990, British Journal of Medicine, vol. 311, No. 7006 (Sep. 9, 1995), pp. 663-666.*
Lowes et al., Pathogenesis and therapy of psoriasis, Nature, vol. 445, 2007, pp. 866-873.*

(Continued)

Primary Examiner — Scott Long
Assistant Examiner — Evelyn Y Pyla
(74) Attorney, Agent, or Firm — Sughrue Mion, PLLC

(57) ABSTRACT

The present invention relates to a mesenchymal stem cell having immunomodulatory activity and a preparation method therefor and, more specifically, to: a rapamycin-treated mesenchymal stem cell having immunomodulatory activity, which expresses any one or more cell surface factors selected from the group consisting of CCR1, CCR2, CCR3, CCR4, CCR7, CCR9 and CXCR4; a cell therapy composition comprising the mesenchymal stem cell, for preventing or treating immune disorders; and a preparation method for the mesenchymal stem cell having immunomodulatory activity. The rapamycin-treated mesenchymal stem cell having immunomodulatory activity, according to the present invention, has increased expression of IDO, TGF-β and IL-10 which are factors having immunomodulatory activity, has decreased expression of Phospho-mTOR, Rictor and Ractor which are signal transduction factors of mTOR, and has increased expression, in the cell, of autophagic inducer Beclin1, ATG5, ATG7, LC3I or LCII. If this cell is used as a cell therapy in individuals having immune disorders, it is possible to effectively treat immune disorders.

4 Claims, 21 Drawing Sheets
Specification includes a Sequence Listing.

(56) References Cited

U.S. PATENT DOCUMENTS

2008/0159998 A1* 7/2008 Ichim .................. C12N 5/0667
424/93.21
2010/0322894 A1 12/2010 Atkinson et al.

OTHER PUBLICATIONS

Mandal et al., Nov. 6, 2012, News Medical Life Sciences, retrieved from the Internet: http://www.news-medical.net/health/Metastasis-Treatment.aspx.*

Jamkhande et al., Saudi Pharmaceutical Journal, 2014, vol. 22, pp. 179-190.*

Davatchi et al., Mesenchymal stem cell therapy for knee osteoarthritis. Preliminary report on four patients, International Journal of Rheumatic Diseases, 2011; 14: 211-215.*

Faghihi et al., The effect of purmorphamine and sirolimus on osteogenic differentiation of human bone marrow-derived mesenchymal stem cells, Biomedicine & Pharmacotherapy, vol. 67 (2013) pp. 31-38.*

AbMole, Rapamycin, retrieved from the internet (Dec. 18, 2017), http://www.abmole.com/products/rapamycin.html.*

Gonzalez et al., Arthritis & Rheumatism, vol. 60, No. 4, Apr. 2009, pp. 1006-1019.*

Macedo et al., Transplantation Research 2012, 1:16, pp. 1-7.*

Albersen et al., Sexual Medicine 2013, 1:3-15.*

Gonzalez-Rey et al., Human adult stem cells derived from adipose tissue protect against experimental colitis and spesis; Gut, 2009, vol. 58: pp. 929-939.*

Body Weight Information for C57Bl/6 mice, retrieved from the internet (Mar. 6, 2019): https://www.jax.org/jax-mice-and-services/strain-data-sheet-pages/body-weight-chart-000664.*

Choi et al., Reversal of Serologic, Immunologic, and Histologic Dysfunction in Mice With Systemic Lupus Erythematosus by Long-Term Serial Adipose Tissue-Derived Mesenchymal Stem Cell Transplantation, Arthritis & Rheumatism, vol. 64, No. 1 Jan. 2012, pp. 243-253.*

Hu et al., Lactobacillus paracasei GMNL-32 exerts a therapeutic effect on cardiac abnormalities in NZB/W F1 mice, PLOS One: 12(9), 2017, pp. 1-14.*

Ge, W. et al., "Infusion of mesenchymal stem cells and rapamycin synergize to attenuate alloimmune responses and promote cardiac allograft tolerance," Am J Transplant, 9(8):1760-72, Aug. 2009.

Buron, F. et al., "Human Mesenchymal Stem Cells and Immunosuppressive Drug Interactions in Allogeneic Responses: An In Vitro Study Using Human Cells," Transplantation Proceedings, 41(8):3347-3352, Oct. 2009.

* cited by examiner

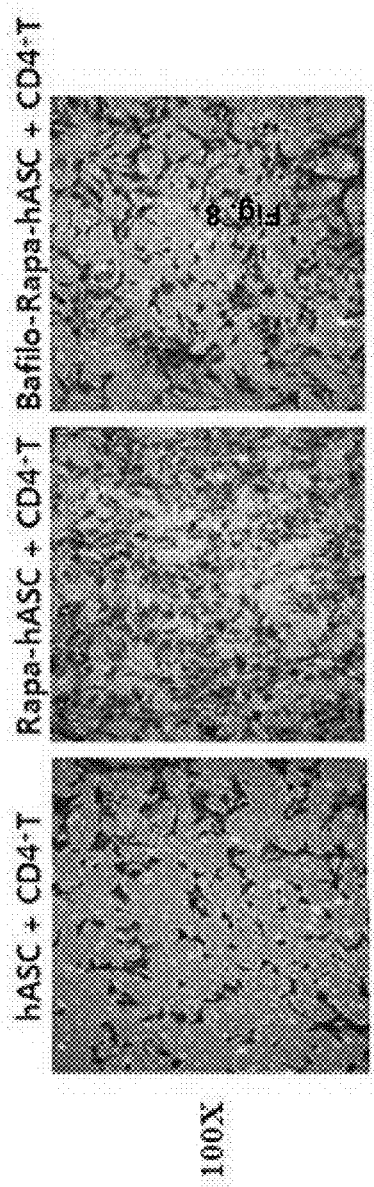
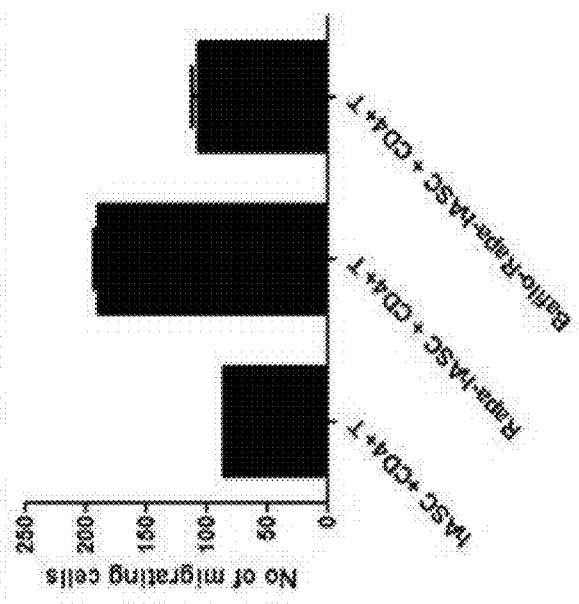
Fig. 8a
Fig. 8b

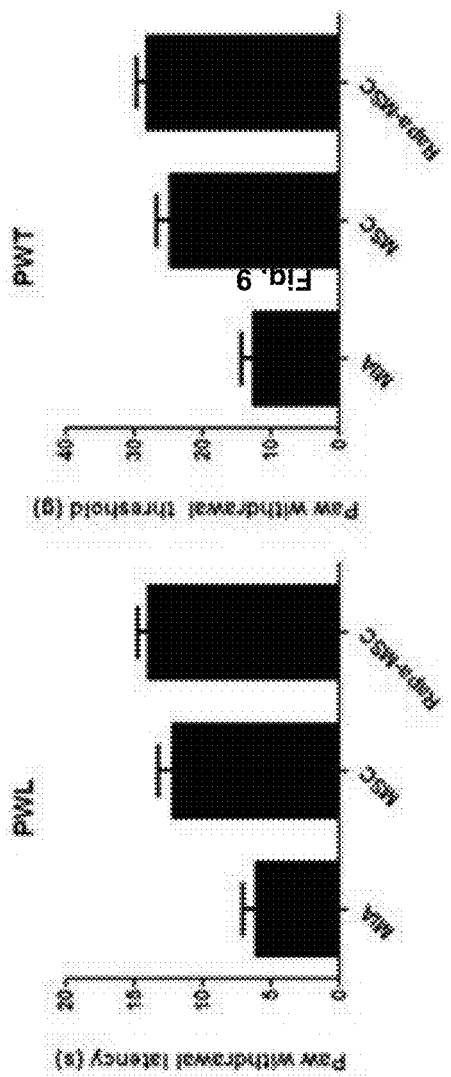
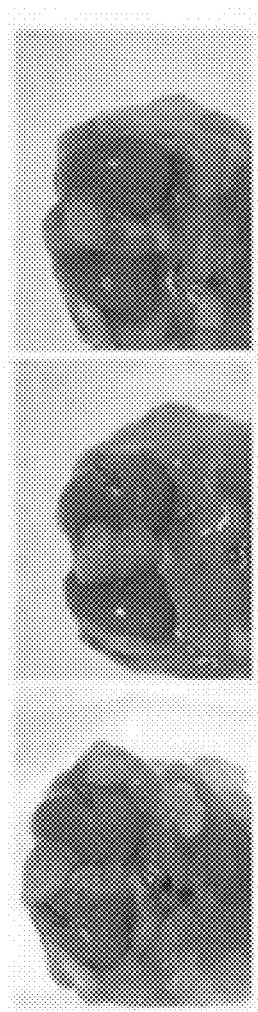
Fig. 9a
Fig. 9b
Fig. 9

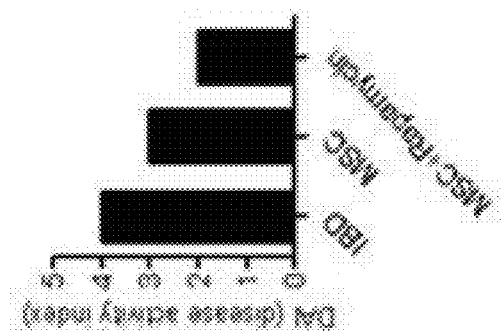
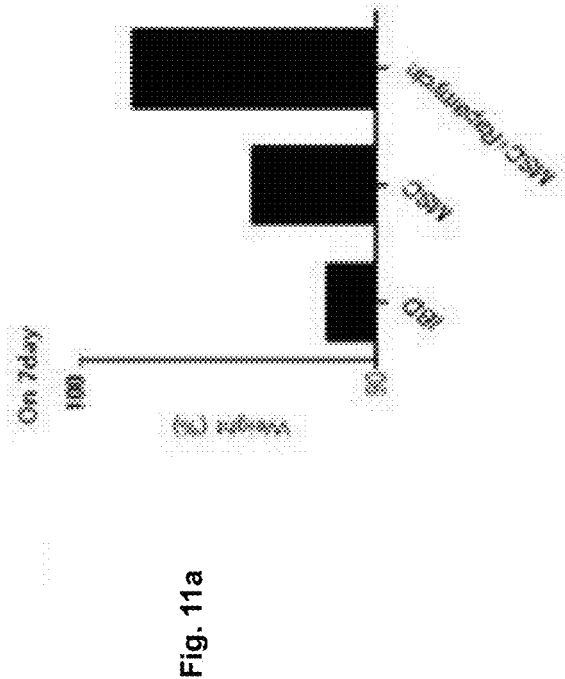
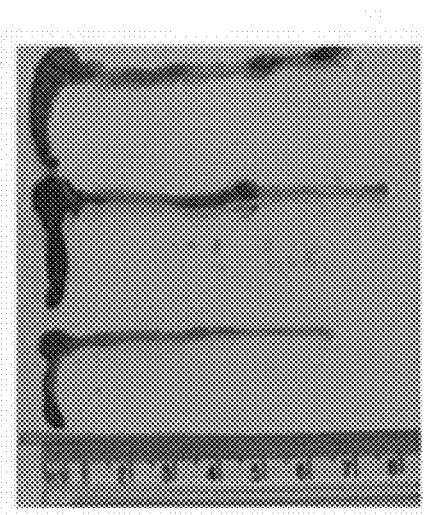
Fig. 11a
Fig. 11b
Fig. 11c

MTOR/STAT3 SIGNAL INHIBITOR-TREATED MESENCHYMAL STEM CELL HAVING IMMUNOMODULATORY ACTIVITY, AND CELL THERAPY COMPOSITION COMPRISING SAME, FOR PREVENTING OR TREATING IMMUNE DISORDERS

TECHNICAL FIELD

The present invention relates to rapamycin-treated mesenchymal stem cells having immunomodulatory activity and a cell therapy composition including the same, for preventing or treating immune disorders.

BACKGROUND ART

Immunity is one of the self-protection systems in the body to respond to all foreign polymer materials (antigens), which invade into or being injected into the living tissues. Lymphocytes, being the major constituting component of the immune system, are leukocytes which are produced in the bone marrow and circulated along with blood into lymphatic tissues, organs, and in particular, lymph nodes, spleens, tonsils, etc. When stimulated by appropriate antigens, B cells rapidly proliferate and form clones, which produce specific antibodies (immunoglobulins) capable of neutralizing the antigens. The antibodies produced by B cells perform a humoral immunity while circulating in the body fluid. T cells are produced in the thymus and transferred to lymphatic tissues, and are responsible for a cell-mediated immunity, which directly attack antigens.

Additionally, one of the most important characteristics in all normal individuals is that they can recognize and respond to non-self antigens, thereby capable of removing the non-self antigens while not harmfully responding to self-antigen materials which constitute themselves. The unresponsiveness of the living body to self-antigens is called immunological unresponsiveness or tolerance. When there is a problem in inducing or continuously maintaining self-tolerance, there occurs an immune response to self-antigens, and as a result, there occurs a phenomenon that attacks self-tissues, thus developing various self-immune disorders.

Meanwhile, the method of treating these self-immune disorders has been mostly relied on using drugs that inhibit the self-immune functions. However, these drugs have limitations in treatment because they cannot be continuously used due to many side effects and thus cannot sufficiently prevent recurrence. Accordingly, new and more effective therapeutic agents to treat the immune disorders have been studied and developed, and recently, research has been focused on the development of a cell therapy, and research has been increasingly focused on the use of stem cells as a cell therapy. In particular, the exact mechanism of action of mesenchymal stem cells among stem cells for the immunomodulatory activity has not been identified and there is almost no research regarding the preparation of stem cells having excellent therapeutic effect for treating immune disorders.

Under these circumstances, the present inventors, while endeavoring to develop a cell therapy for effective immunological treatment using stem cells, have discovered that rapamycin-treated mesenchymal stem cells have excellent therapeutic effect for treating immune disorders, thereby completing the present invention.

DISCLOSURE

Technical Problem

Accordingly, the present invention is directed to providing a rapamycin-treated mesenchymal stem cell having immunomodulatory activity, which expresses any one or more cell surface factors selected from the group consisting of CCR1, CCR2, CCR3, CCR4, CCR7, CCR9, and CXCR4.

Additionally, the present invention is also directed to providing a cell therapy composition for preventing or treating immune disorders containing the mesenchymal stem cell having immunomodulatory activity according to the present invention as an active ingredient.

Additionally, the present invention is also directed to providing a method for preparing the mesenchymal stem cell having the immunomodulatory activity.

Technical Solution

In order to achieve the above objects, one aspect of the present invention provides a rapamycin-treated mesenchymal stem cell having immunomodulatory activity, which expresses any one or more cell surface factors selected from the group consisting of CCR1, CCR2, CCR3, CCR4, CCR7, CCR9, and CXCR4.

In an exemplary embodiment of the present invention, the mesenchymal stem cell may be isolated from peripheral blood or adipose tissue.

In another exemplary embodiment of the present invention, the mesenchymal stem cell may be treated with rapamycin at a concentration of 10 nM to 100 nM based on $2.5 \times 10^5$ to $7.5 \times 10^5$ of the mesenchymal stem cells.

In still another exemplary embodiment of the present invention, the mesenchymal stem cell may have increased expression of any one or more factors selected from the group consisting of indole 2,3-dioxygenase (IDO), transforming growth factor beta (TGF-β), and IL-10, by the rapamycin treatment.

In still another exemplary embodiment of the present invention, the mesenchymal stem cell may have decreased expression, in the cell, of Phospho-mTOR, Rictor, and Ractor, which are signal transduction factors of mTOR, by the rapamycin treatment.

In still another exemplary embodiment of the present invention, the mesenchymal stem cell may have increased expression, in the mesenchymal stem cell, of any one or more autophagic inducers selected from the group consisting of Beclin1, ATG5, ATG7, LC3I, and LCII, by the rapamycin treatment.

Another aspect of the present invention provides a cell therapy composition for preventing or treating immune disorders containing the mesenchymal stem cell having immunomodulatory activity according to the present invention as an active ingredient.

In an exemplary embodiment of the present invention, the composition may be administered in an amount from $1 \times 10^6$ to $5 \times 10^7$ mesenchymal stem cells having immunomodulatory activity per kg of the body weight of a subject to be administered.

In another exemplary embodiment of the present invention, the immune disorders may be selected from the group consisting of osteoarthritis, rheumatoid arthritis, asthma, dermatitis, psoriasis, cystic fibrosis, post transplantation late and chronic solid organ rejection, graft-versus-host disease, transplant rejection disease, multiple sclerosis, systemic lupus erythematosus, Sjogren syndrome, Hashimoto thyroiditis, polymyositis, scleroderma, Addison disease, vitiligo, pernicious anemia, glomerulonephritis, pulmonary fibrosis, inflammatory bowel disease, Crohn's disease, autoimmune diabetes, diabetic retinopathy, rhinitis, ischemia-reperfusion injury, post-angioplasty restenosis, chronic obstructive pulmonary disease (COPD), Graves' disease, gastrointestinal allergy, conjunctivitis, atherosclerosis, coronary artery disease, angina, cancer metastasis, small artery disease, and mitochondrial disease.

A further aspect of the present invention provides a method of preparing a mesenchymal stem cell, which expresses any one or more cell surface factors selected from the group consisting of CCR1, CCR2, CCR3, CCR4, CCR7, CCR9, and CXCR4, including: treating the mesenchymal stem cells in an amount of $2.5 \times 10^5$ cells to $7.5 \times 10^5$ cells isolated from peripheral blood or adipose tissue with rapamycin at a concentration of 10 nM to 100 nM; and culturing the treated cells at from 28° C. to 42° C. for from 18 hours to 27 hours.

Additionally, the present invention provides a method of preparing a mesenchymal stem cell, which expresses any one or more cell surface factors selected from the group consisting of CCR1, CCR2, CCR3, CCR4, CCR7, CCR9, and CXCR4, including treating the mesenchymal stem cells, in an amount of $2.5 \times 10^5$ cells to $7.5 \times 10^5$ cells isolated from peripheral blood or adipose tissue, with rapamycin at a concentration of from 10 nM to 100 nM; and culturing the treated cells at from 28° C. to 42° C. for from 18 hours to 27 hours.

Additionally, the present invention provides a method of treating immune disorders including administering a mesenchymal stem cell having immunomodulatory activity prepared according to the method of the present invention to a subject in need thereof.

Additionally, the present invention provides a method of promoting the expression of any one or more cell surface factors selected from the group consisting of CCR1, CCR2, CCR3, CCR4, CCR7, CCR9, and CXCR4, in a mesenchymal stem cell, including treating the mesenchymal stem cells, in an amount of $2.5 \times 10^5$ cells to $7.5 \times 10^5$ cells isolated from peripheral blood or adipose tissue, with rapamycin at a concentration of from 10 nM to 100 nM; and culturing the treated cells at from 28° C. to 42° C. for from 18 hours to 27 hours.

Advantageous Effects

The present invention relates to a rapamycin-treated mesenchymal stem cell having immunomodulatory activity, which expresses any one or more cell surface factors selected from the group consisting of CCR1, CCR2, CCR3, CCR4, CCR7, CCR9, and CXCR4; a cell therapy composition for preventing or treating immune disorders containing the mesenchymal stem cell having immunomodulatory activity; and a method of preparing the mesenchymal stem cell having immunomodulatory activity. The rapamycin-treated mesenchymal stem cell having immunomodulatory activity, according to the present invention, has increased expression of IDO, TGF-β, and IL-10 which are factors having immunomodulatory activity, has decreased expression of Phospho-mTOR, Rictor and Ractor which are signal transduction factors of mTOR, and has increased expression, in the mesenchymal stem cell, of autophagic inducer Beclin1, ATG5, ATG7, LC3I, or LCII. Accordingly, the use of the mesenchymal stem cell as a cell therapy in individuals having immune disorders can effectively treat immune disorders.

DESCRIPTION OF DRAWINGS

FIGS. 8a and 8b show the analysis result of degree of cell migration of the mesenchymal stem cell derived from human adipose tissues prepared by rapamycin treatment obtained using cell migration analysis kit, in which FIG. 8a shows the degree of staining of the migrated cells observed under a microscope, and FIG. 8b shows the graph illustrating the counted number of migrated cells.

FIG. 9a shows the result of pain analysis in a mouse model induced with osteoarthritis in a group injected with mesenchymal stem cells derived from human adipose tissues prepared by rapamycin treatment (Rapa-MSC), a group injected with only mesenchymal stem cell (MSC), a group with no treatment at all (MIA), and a group with a normal mouse (Normal), and FIG. 9b shows the images of degree of cartilage damage observed after staining via India ink staining method.

FIGS. 11A, 11B and 11C show the result of a therapeutic effect of rapamycin-treated mesenchymal stem cells in a mouse model with inflammatory bowel disease.

MODES OF THE INVENTION

Figure 1B:
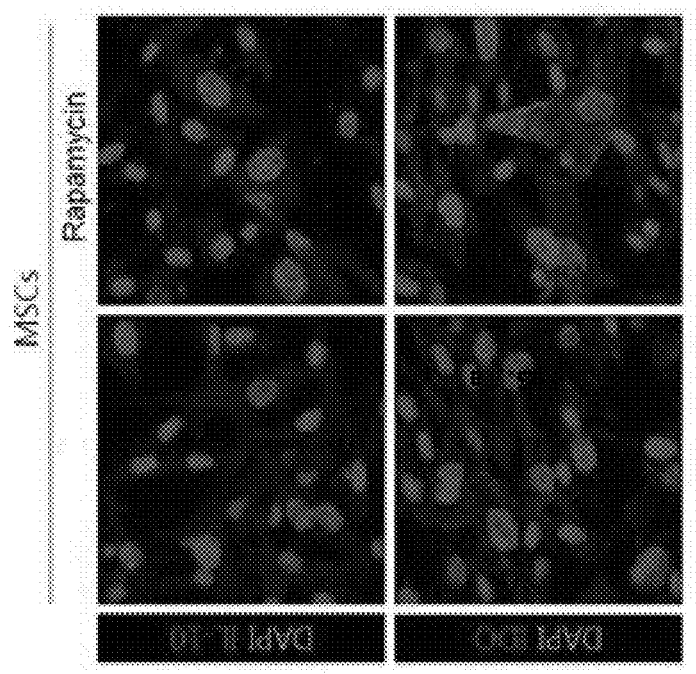
FIG. 1b shows the images observed under fluorescence microscope of the expression amount of IDO and IL-10 expressed in the mesenchymal stem cells derived from human adipose tissue prepared by rapamycin treatment.

Hereinafter, exemplary embodiments of the present invention will be described in detail. However, the present invention is not limited to the exemplary embodiments disclosed below, but can be implemented in various forms. The following exemplary embodiments are described in order to enable those of ordinary skill in the art to embody and practice the invention.

The present invention is characterized in providing a rapamycin-treated mesenchymal stem cell having immunomodulatory activity, in which any one or more cell surface factors selected from the group consisting of CCR1 (C-C chemokine receptor type 1), CCR2 (C-C chemokine receptor type 2), CCR3 (C-C chemokine receptor type 3), CCR4 (C-C chemokine receptor type 4), CCR7 (C-C chemokine receptor type 7), CCR9 (C-C chemokine receptor type 9), and CXCR4 (C-X-C chemokine receptor type 4) are expressed.

The present invention is characterized in treating a mesenchymal stem cell with rapamycin of Formula 1 below, and the IUPAC nomenclature of rapamycin is (3S,6R,7E,9R,10R,12R,14S,15E,17E,19E,21S,23S,26R,27R,34aS)-9,10,12,13,14,21,22,23,24,25,26,27,32,33,34,34a-hexadecahydro-9,27-dihydroxy-3-[(1R)-2-[(1S,3R,4R)-4-hydroxy-3-methoxycyclohexyl]-1-methylethyl]-10,21-dimethoxy-6,8,12,14,20,26-hexamethyl-23,27-epoxy-3H-pyrido [2,1-c][1,4]-oxaazacyclohentriacontine-1,5,11,28,29 (4H,6H,31H)-pentone, and its molecular formula is $C_{51}H_{79}NO_{13}$, and has a molecular weight of 914.172.

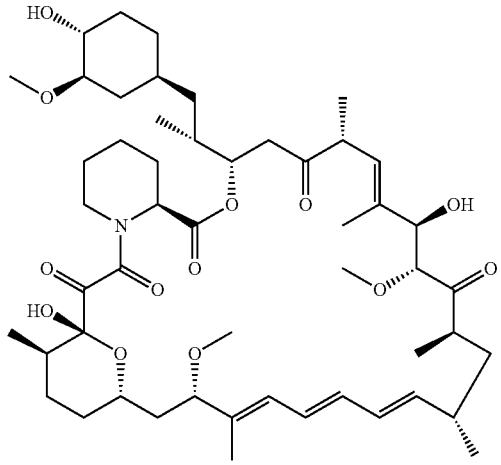

<Formula 1>

The present inventors, while endeavoring to develop a cell therapy for treating immune disorders, have discovered by experiments that mesenchymal stem cells prepared by rapamycin treatment have excellent therapeutic effect for treating immune disorders compared to those not treated with rapamycin.

Accordingly, the present invention can provide a rapamycin-treated mesenchymal stem cell having immunomodulatory activity, and can provide a cell therapy composition for preventing or treating immune disorders containing the mesenchymal stem cell having immunomodulatory activity as an active ingredient.

The mesenchymal stem cell (MSC) is a stem cell that can be isolated from bone marrow, blood, dermis, periosteum, etc., and it is a pluripotent or multipotent cell which can be differentiated into an adipocyte, a chondrocyte, an osteocyte, etc.

In particular, the mesenchymal stem cell used in the present invention may be a mesenchymal stem cell from an animal, preferably from a mammal, and more preferably a human mesenchymal stem cell. Additionally, the mesenchymal stem cell of the present invention may be those derived from bone marrow, adipose tissue, peripheral blood, livers, lungs, amniotic fluid, chorionic membrane of placenta, or umbilical cord blood, and preferably those derived from adipose tissue or peripheral blood may be used.

For reference, mesenchymal stem cells may be obtained from various sources as described above, and the specific process for obtaining the mesenchymal stem cell may be explained as follows: (1) isolating a mesenchymal stem cell from a mammal including human or mice, preferably a human mesenchymal stem cell source, e.g., blood, bone marrow or adipose tissue; (2) culturing the isolated cell in an appropriate medium; and (3) removing the suspension cells during culture and subculturing the cells adhered to the culture plates, thereby finally obtaining the established mesenchymal stem cell.

The medium used in the above process may be any conventional medium used in the culture of stem cells. Preferably, the medium may be a medium containing serum (e.g., fetal bovine serum, horse serum, and human serum). The medium that can be used in the present invention may include, for example, RPMI series, Eagle's MEM, α-MEM, Iscove's MEM, 199 medium, CMRL 1066, RPMI 1640, F12, F10, Dulbecco's modification of Eagle's medium (DMEM), a mixture of DMEM and F12, Way-mouth's MB752/1, McCoy's 5A, and MCDB series, but is not limited thereto.

The medium may contain other ingredients such as antibiotics or antifungals (e.g., penicillin, streptomycin), and glutamine, etc. Additionally, the confirmation of the isolated and cultured mesenchymal stem cell may be performed by flow cytometry. The cytometry analysis may be performed using specific surface markers of mesenchymal stem cells. For example, mesenchymal stem cells show a positive response to CD44, CD29 and/or MHC class I and thus mesenchymal stem cells can be confirmed by the same.

Meanwhile, in the present invention, for the purpose of using the mesenchymal stem cells derived from various sources for the treatment of immune disorders, a novel mesenchymal stem cell having immunomodulatory activity was prepared by treating with rapamycin.

Rapamycin is a compound well known as an antibiotic, which was first discovered in a microorganism, *Streptomyces*, and was discovered in Easter Island, famous for massive statues. Rapamycin is known to have an effect of inhibiting cell division of fungi, and was later known to have an immunuosuppressive effect. Additionally, it is known recently that rapamycin has an anticancer activity.

Figure 1A:
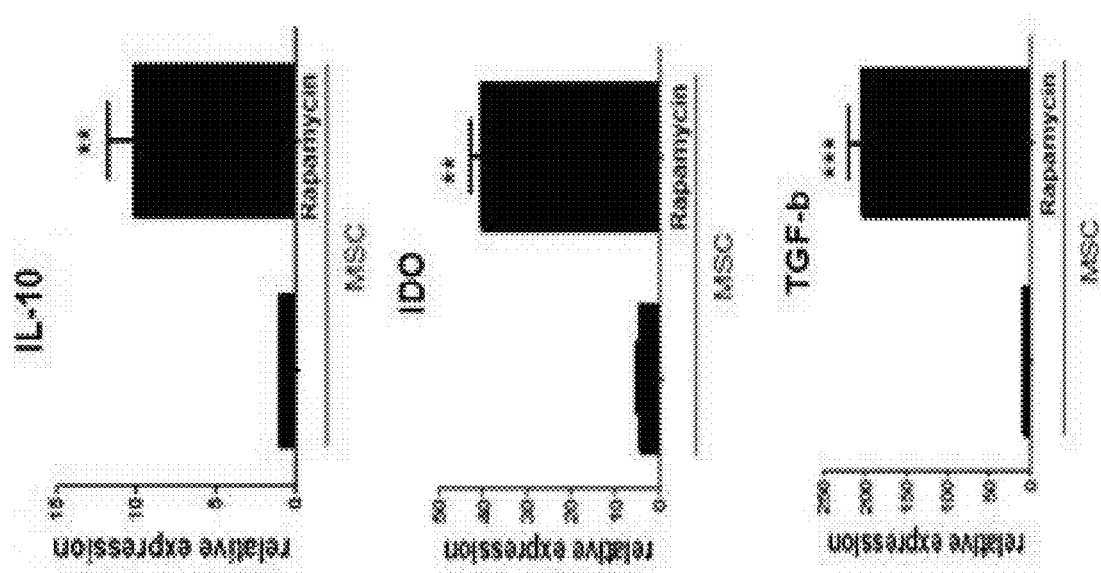
FIG. 1a shows the analysis results of expression levels of IL-10, IDO, and TGF-β expressed in the cells after rapamycin-treatment of the mesenchymal stem cells isolated from peripheral blood.

Under these circumstances, the present inventors, for the development of a novel therapeutic agent for treating immune disorders using rapamycin and mesenchymal stem cells, have treated mesenchymal stem cells with rapamycin, and as a result, it was confirmed that the mesenchymal stem cells cultured after rapamycin treatment showed a significant increase in expression of TGF-β, IDO, and IL-10 genes, which are associated with the immunomodulatory activity in the cell (refer to FIGS. 1a and 1b).

More specifically, with respect to the TGF-β, IDO, and IL-10 genes associated with the immunomodulatory activity, transforming growth factor β (TGF-β) can promote or inhibit the growth of cells and is known to have an immunomodulatory activity. In the experiment of the present invention, the rapamycin-treated mesenchymal stem cells derived from adipose tissue was confirmed to have almost a 30-fold increase in TGF-β expression compared to those not treated with rapamycin.

Additionally, indoleamine 2,3-dioxygenase (IDO) is known to be a factor capable of measuring the functions and activities in the immune system, and recently, it is known to have an anti-inflammatory effect along with IL-10.

Figure 6A:
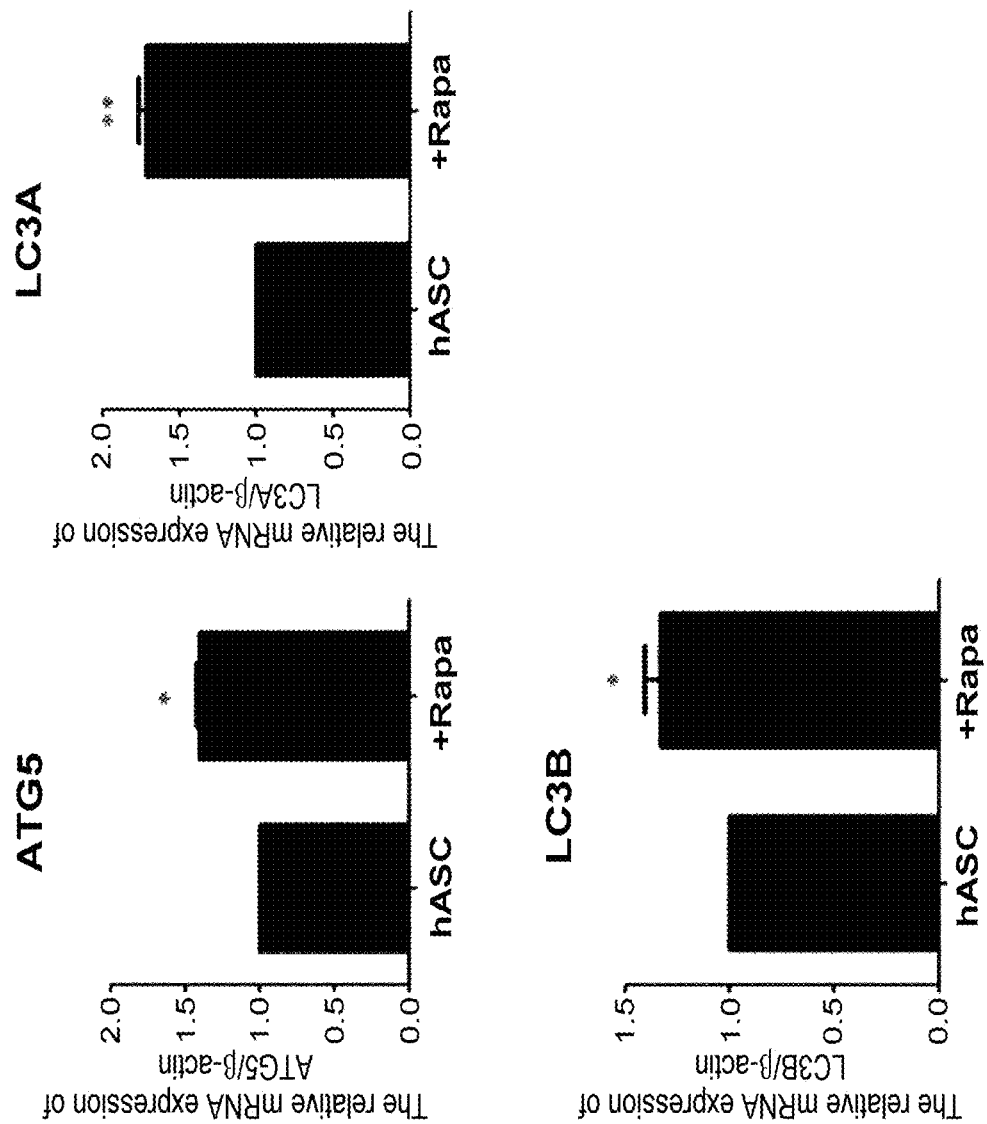
FIGS. 6a to 6c respectively show the analysis result by RT-PCR of the mRNA expression levels of ATG5, LC3A, and LC3B, which are factors involved in phagocytic actions, in the mesenchymal stem cells derived from human adipose tissues prepared by rapamycin treatment (FIG. 6a), the digitized result of expression amount of each of the factors (FIG. 6b), and the images of western blot analysis of expression amount of each of the factors involved in phagocytic actions (FIG. 6c).
Figure 6B:
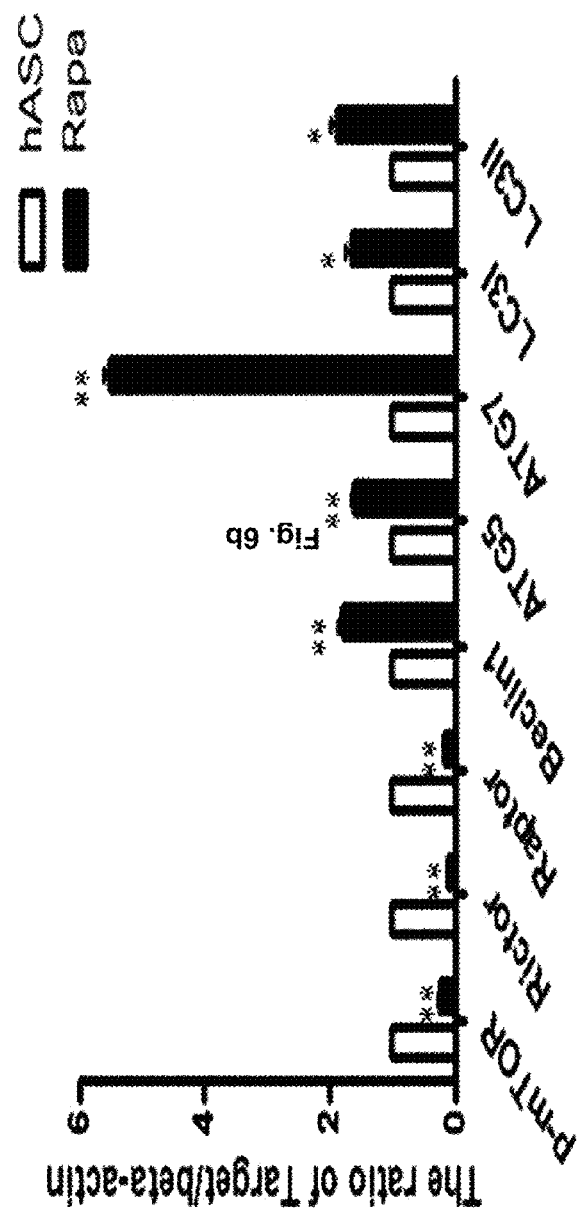
Figure 6C:
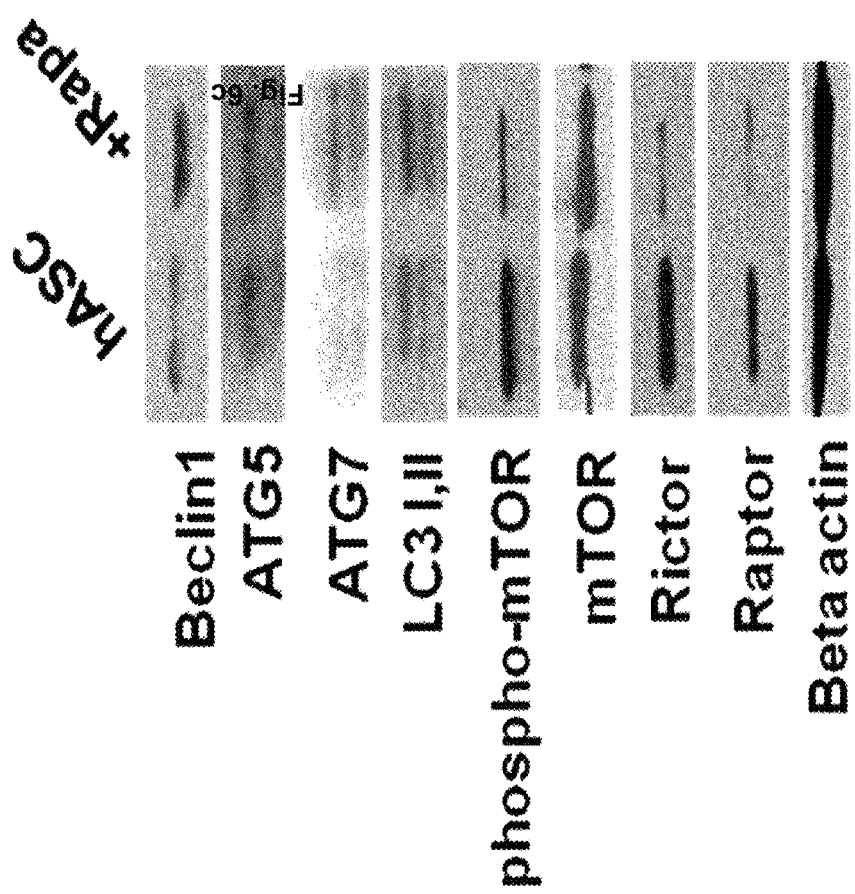

Furthermore, the mesenchymal stem cell of the present invention prepared by treating with rapamycin was shown to have increased expressions of genes involved in autophagy, and also that the signaling of mTOR is inhibited in these cells (refer to FIGS. 6a and 6c).

Autophagy is a process of decomposing small organs or cellular components of a self by bacteria and differs from heterophagy, which intakes exogenous polymers via intracellular digestion such as pinocytosis and phagocytosis. Cells act to remove unnecessary cellular components during the processes of decomposing self-proteins by responding to the deficiency in nutrients or reestablishment of cells, and cell components form phagocytic vacuoles by being encompassed by membranes derived from endoplasmic reticulum, and they also fuse with lysosomes to form autophagolysosomes for decomposition.

Additionally, since the autophagy has the effects of controlling beneficial or harmful effects of immune and inflammation, and the effects of preventing infectious diseases, and self-immunization and inflammation diseases, the rapamycin-treated mesenchymal stem cells of the present invention have an autophagy, and thus may be more useful for the immunity and treatment of inflammation.

Furthermore, in the present invention, to confirm whether the therapeutic effect of the rapamycin-treated mesenchymal stem cell is associated with the inhibition of mTOR signaling, the phosphorylation level of active type of mTOR was analyzed, and as a result, it was shown that the phosphorylation level of mTOR was reduced when treated with rapamycin, and also the expression of Rictor and Ractor was shown to be decreased.

Meanwhile, mTOR signaling pathway is very important in controlling protein synthesis, and is known to be activated in various cancer cells. Hsieh et al. have already identified that several genes involved in the invasion of cancer cells in prostate cancer cells and prostate cancer in a mouse are controlled by mTOR. Additionally, it has been reported that the inhibition of mTOR signaling not only has the effect on tumor cells but also has a broad control effect on immune cells, and in particular, the inhibition of mTOR is known to be directly linked to the effect of immunosuppression.

Accordingly, in the present invention, the mTOR signaling is inhibited in the mesenchymal stem cell by the rapamycin treatment.

Figure 7:
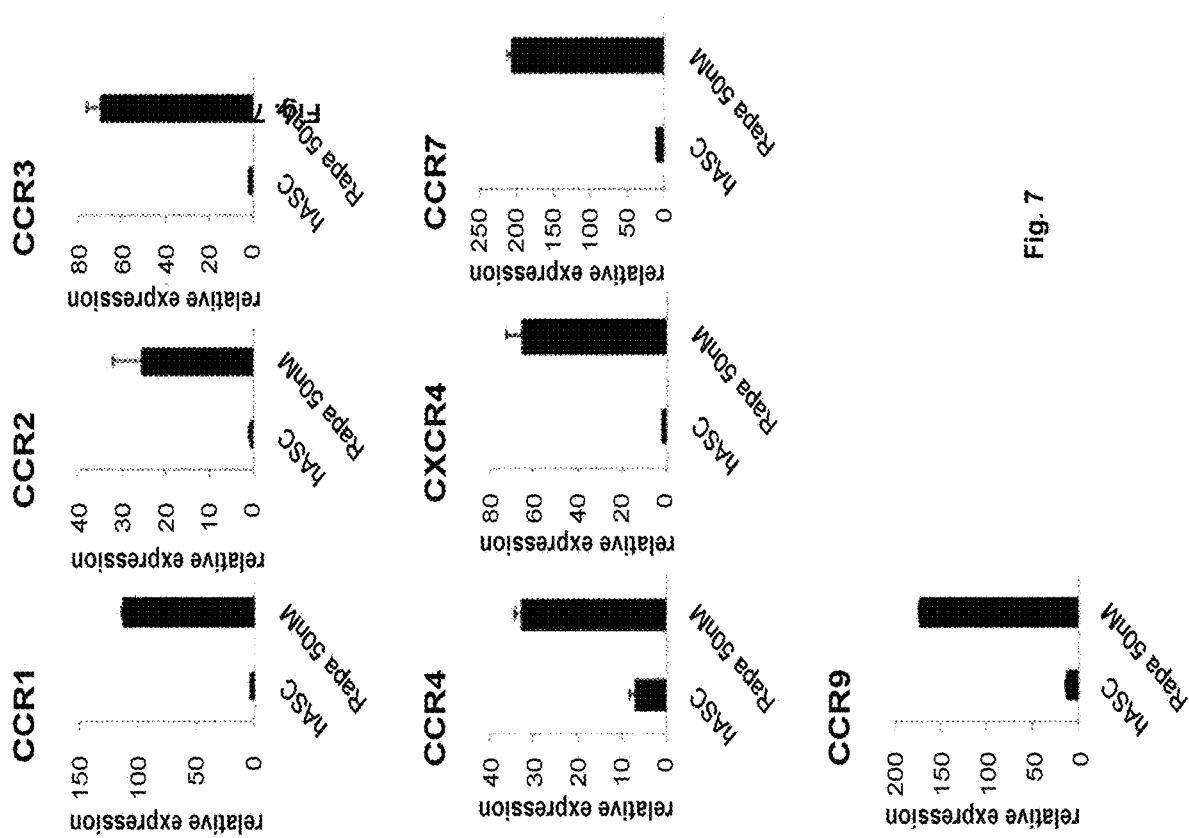
FIG. 7 shows the comparison result of expression levels of factors involved in cell migration, which are expressed on the cell surface of the mesenchymal stem cell derived from human adipose tissues prepared by rapamycin treatment.

Additionally, the present inventors have examined whether the mesenchymal stem cells prepared by rapamycin treatment has the property of cell migration, and as a result, the rapamycin-treated mesenchymal stem cells were shown to have an increased expression of chemokines associated with cell migration in the cells (refer to FIGS. 7 and 8).

As such, the present inventors were able to predict that the use of the mesenchymal stem cell according to the present invention as a cell therapy enables an efficient migration of cells to a lesion area to be targeted thereby drawing out therapeutic effects at the target area.

The mesenchymal stem cell having immunomodulatory activity prepared in the present invention may be prepared by treating mesenchymal stem cells in the range of from $1 \times 10^6$ to $5 \times 10^7$ cells per kg of a subject to be administered with rapamycin at a concentration of 10 nM to 100 nM, and more preferably, by treating $5 \times 10^5$ mesenchymal stem cells isolated from peripheral blood or adipose tissue with 100 nM rapamycin followed by culturing at a temperature from 28° C. to 42° C. for 18 hours to 27 hours.

Additionally, the present invention may provide a cell therapy composition for preventing or treating immune disorders containing the mesenchymal stem cell having immunomodulatory activity as an active ingredient.

As used herein, the term "cell therapy" refers to a pharmaceutical drug which can be used for the purpose of treatment, diagnosis, and prevention through a series of actions which can change the biological characteristics of cells by extracellular propagation, selection, or other methods of living autologous, allogenic, and xenogenic cells in order to restore the functions of cells and tissues. The cell therapies have been controlled as pharmaceutical drugs in the U.S. since 1993 and in Korea since 2002. The cell therapies may be largely classified into two types: first, a stem cell therapy for tissue regeneration or restoring organ functions, and second, for the control of immune responses such as inhibition or exacerbation of immune responses in the body.

The cell therapy composition of the present invention may be administered via any conventional route as long as it enables the arrival at the target tissue. A parenteral administration, e.g., intraperitoneal administration, intravenous administration, intramuscular administration, subcutaneous administration, and intradermal administration, but is not limited thereto.

The composition may be formulated in an appropriate form along with a pharmaceutically acceptable carrier commonly used in cell therapies. As used herein, the term "pharmaceutically acceptable" refers to a composition which does not conventionally cause any allergic reactions such as gastrointestinal disorder and dizziness, etc., or similar reactions thereof when physiologically accepted and administered to humans. Examples of pharmaceutically acceptable carriers may include carriers for parenteral administration such as water, appropriate oils, saline, aqueous glucose, and glycol, and may further include a stabilizer and a preservative. Examples of appropriate stabilizers may include sodium bisulfite, sodium sulfite, or an antioxidant such as ascorbic acid. Examples of appropriate preservatives may include benzalkonium chloride, methyl- or propylparaben and chlorobutanol. Examples of other pharmaceutically acceptable carriers may be referred to those described in the following reference (Remington's Pharmaceutical Sciences, 19th ed., Mack Publishing Company, Easton, Pa., 1995).

Additionally, the above composition may be administered by a random device capable of transporting cell therapies into target cells.

The cell therapy composition of the present invention may contain a therapeutically effective amount of cell therapies for the treatment of diseases. As used herein, the term "therapeutically effective amount" refers to the amount of an active ingredient or a pharmaceutical composition which can induce a biological or medical reaction in systems, animals, or humans that can be thought by researchers, veterinarians, doctors, or other clinical studies, and it includes the amount that can induce the alleviation of the symptoms of diseases or disorders to be treated. It is obvious that the cell therapies to be included in the composition of the present invention can vary according to the desired effects. Accordingly, the optimal amount of cell therapies may be easily determined by one of ordinary skills in the art, and may be controlled by various factors, such as types of diseases, severity of diseases, contents of other ingredients contained in the composition, types of formulations, age, weight, general health conditions, sex, and diet of a patient, administration time, administration routes, release rate of composition, treatment period, and drugs used simultaneously. It is important to include the amount that may exhibit the maximum effect with a minimum amount without any adverse effects, in consideration of all the above factors. For example, the composition of the present invention may include mesenchymal stem cells having immunomodulatory activity in the amount of from $1\times10^6$ to $5\times10^7$ cells per kg of body weight as cell therapies.

Additionally, the present invention provides a method for preventing or treating immune disorders including administering the cell therapy composition of the present invention in a therapeutically effectively amount to a mammal. In particular, as used herein, the term "mammals" refers to mammals as a subject for treatment, observation, or experiments, and preferably humans.

In the treatment method of the present invention, for adults, the cell therapy included in a composition may preferably include $1\times10^4$ to $1\times10^8$ cells per kg of the body weight when the cell therapy composition of the present invention is administered once daily or several divided doses daily.

In the treatment method of the present invention, the composition containing the cell therapy of the present invention as an active ingredient may be administered via intrarectal-, intravenous-(IV), intraarterial-, intraperitoneal-, intramuscular-, intrasternal-, dermal-, topical-, intravitreal-, or intradermal routes, by a conventional method.

Additionally, the immune disorders to be treated by the rapamycin-treated mesenchymal stem cell and the cell therapy compositions containing the same may include osteoarthritis, rheumatoid arthritis, asthma, dermatitis, psoriasis, cystic fibrosis, post transplantation late and chronic solid organ rejection, graft-versus-host disease, transplant rejection disease, multiple sclerosis, systemic lupus erythematosus, Sjogren syndrome, Hashimoto thyroiditis, polymyositis, scleroderma, Addison disease, vitiligo, pernicious anemia, glomerulonephritis, pulmonary fibrosis, inflammatory bowel disease, Crohn's disease, autoimmune diabetes, diabetic retinopathy, rhinitis, ischemia-reperfusion injury, post-angioplasty restenosis, chronic obstructive pulmonary disease (COPD), Graves' disease, gastrointestinal allergy, conjunctivitis, atherosclerosis, coronary artery disease, angina, cancer metastasis, small artery disease, and mitochondrial disease, although not limited thereto.

The advantages and characteristics of the present invention and the methods to achieve these will be more clearly understood from the following detailed description when taken in conjunction with the accompanying examples. Hereinafter, the present invention will be described in more detail with reference to the following Examples. However, these Examples are for illustrative purposes only, and the invention is not intended to be limited by these Examples.

<Example 1> Analysis of Changes in Expression of Genes Associated with Immunomodulatory Activity in Rapamycin-Treated Mesenchymal Stem Cells <1-1> Isolation of Mesenchymal Stem Cells from Peripheral Blood and Culturing Thereof Monocytes were isolated from peripheral blood using Ficoll-paque, cultured in Dulbecco's modified Eagle's medium (DMEM) containing 20% fetal bovine serum for 6 days, and the suspension cells floated to the top were removed, and subcultures were proceeded using only those cells adhered to the cell culture plates at 37° C. (5% $CO_2$). The mesenchymal stem cells were isolated from peripheral blood and cultured while replacing the culture broth at intervals of 3 days.

<1-2> Isolation of Mesenchymal Stem Cells from Adipose Tissue and Culturing Thereof The adipose tissues obtained by liposuction or surgical operation were washed 10 times with PBS containing penicillin-streptomycin to remove blood and impurities, and the tissues were minced to have a weight of from 0.2 g to 0.3 g. The minced tissues were added into a 0.2% collagenase (Roche, Sandhofer Strasse, Mannheim, Germany) solution, and reacted in a 37° C. water bath at 100 rpm for 1 hour. The solution layer decomposed by collagenase and the undecomposed slices were separated using a 100 μm mesh, and the separated collagenase solution was added with an equal amount of PBS. Then, the resultant was centrifuged at 4° C. at 1200 rpm for 5 minutes and the lipid and adipose layer in the supernatant were removed and then the supernatant of collagenase was removed. To remove the remaining collagenase solution from the settled MSC, mesenchymal stem cell growth media [MSCGM: MSC basal medium (Cambrex, Walkersville, Md., USA), mesenchyme cell growth supplement (Cambrex, Walkersville, Md., USA), 4 mM L-glutamine and penicillin (0.025 unit/500 mL)/streptomycin (0.025 mg/500 mL)] was added thereto and the mixture was centrifuged again at 4° C. at 1200 rpm for 5 minutes. MSCGM is a medium based on DMEM containing fetal bovine serum. Then, the supernatant was discarded and the thus-obtained MSC was seeded into a culture dish and cultured in a homeostat at 37° C. (5% $CO_2$) using MSCGM. The culture was performed while replacing the culture broth every two days.

<1-3> Analysis of Expression Level of Genes Associated with Immunomodulatory Activity The mesenchymal stem cells isolated and cultured in <Example 1> were treated with rapamycin, respectively, and the changes in the expression of IDO, IL-10, and TGF-β, which are genes associated with immunomodulatory activity. First, in a condition of 60 mm dish, for the adipose tissue-derived mesenchymal stem cells, the mesenchymal stem cells in the amount of $5\times10^5$ cells which were treated with 100 nM rapamycin and cultured at 37° C. were used. In particular, the mesenchymal stem cells not treated with rapamycin were used as a control, and the expression level of the genes having immunomodulatory activity in rapamycin-treated mesenchymal stem cells was analyzed using a real time PCR method.

As a result of the analysis, as shown in FIGS. 1a and 1b, the mesenchymal stem cells in the group treated with rapamycin showed about a 5-fold increase in the expression of IL-10, IDO, and TGF-β, compared to the group not treated with rapamycin, respectively (FIG. 1a). Additionally, As a result of the analysis under fluorescence microscope, the expression level of IL-10 cytokine was also significantly increased (FIG. 1b).

Accordingly, based on these results, the present inventors have confirmed that the mesenchymal stem cells treated with rapamycin showed a significant increase in the expression of IL-10, IDO, and TGF-β, compared to those cells not treated with rapamycin <Example 2> Analysis of the Inhibitory Effect of Etiological Th17 Cell Growth in Rapamycin-Treated Mesenchymal Stem Cells The present inventors examined the T cell proliferation by thymidine treatment for the investigation of the inhibitory effect of rapamycin-treated mesenchymal stem cells on T cell proliferation. First, mouse CD4+T cells ($1\times10^5$) and mesenchymal stem cells ($1\times10^4$) were added into a 96-well plate in a 1:10 ratio and co-cultured at 37° C. for 3 days. After 3 days, the T cell proliferation was examined by thymidine treatment and thereby analyzed the inhibitory effect against T cell proliferation.

Figure 2:
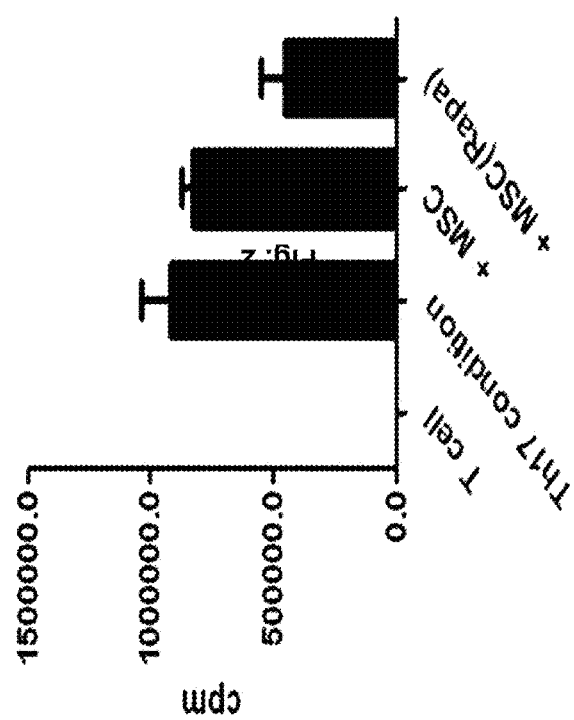
FIG. 2 shows the analysis results of etiological Th17 cell proliferation inhibitory effect of mesenchymal stem cells.

As a result of the analysis, it was confirmed that the inhibitory effect of mesenchymal stem cells on T cell proliferation was further decreased by the rapamycin-treated mesenchymal stem cells (FIG. 2).

<Example 3> Analysis of the Inhibitory Effect of Rapamycin-Treated Mesenchymal Stem Cells Against Inflammatory Factors and Tumor Factors The mesenchymal stem cells isolated and cultured in <Example 1> were treated with rapamycin, respectively, and the changes in the expression of High-mobility group protein B1 (HMGB-1), IL-6, and IL-1β, which are genes associated with inflammatory factors and tumor factors. First, in a condition of 60 mm dish, for the adipose tissue-derived mesenchymal stem cells, the mesenchymal stem cells in the amount of $5\times10^5$ cells which were treated with 100 nM rapamycin and cultured at 37° C. were used. In particular, the mesenchymal stem cells not treated with rapamycin were used as a control, and the expression level of the genes having immunomodulatory activity in rapamycin-treated mesenchymal stem cells was analyzed using a real time PCR method.

Figure 3:
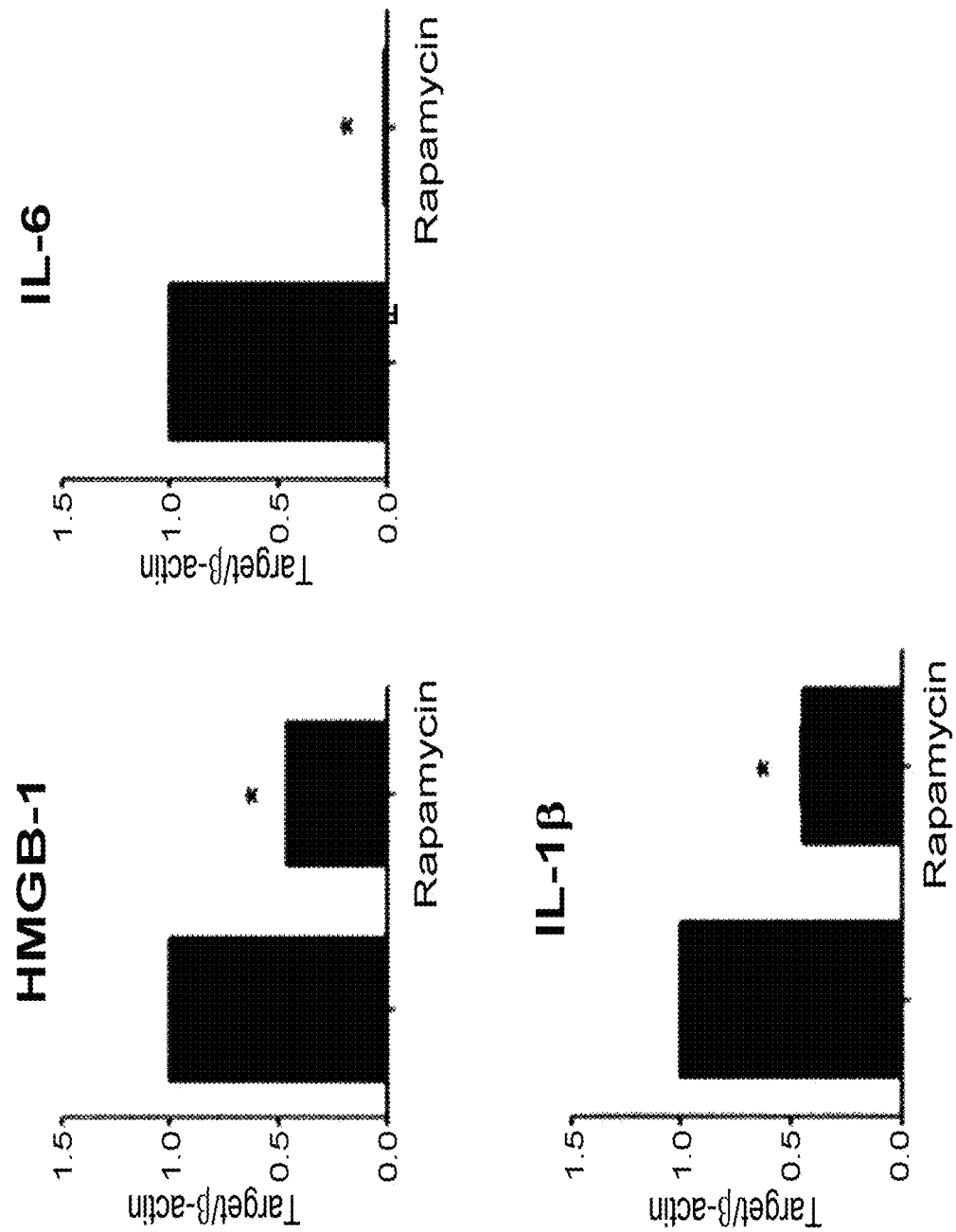
FIG. 3 shows the analysis results of the changes in expression levels of HMGB-1, IL-6, and IL-1β in mesenchymal stem cells treated with rapamycin.

As a result of the analysis, as shown in FIG. 3, the mesenchymal stem cells in the group treated with rapamycin showed a significant decrease in the expression of HMGB-1, IL-6, and IL-1β, compared to the group not treated with rapamycin, respectively.

<Example 4> Analysis of Cell Phenotype CD Markers in Rapamycin-Treated Mesenchymal Stem Cells The mesenchymal stem cells isolated and cultured in <Example 1> were treated with rapamycin, respectively, and the phenotypes of the mesenchymal stem cells were analyzed. In particular, the mesenchymal stem cells not treated with rapamycin were used as a control, and the expression level of cell markers in the rapamycin-treated mesenchymal stem cells were analyzed via flow cytometry.

Figure 4:
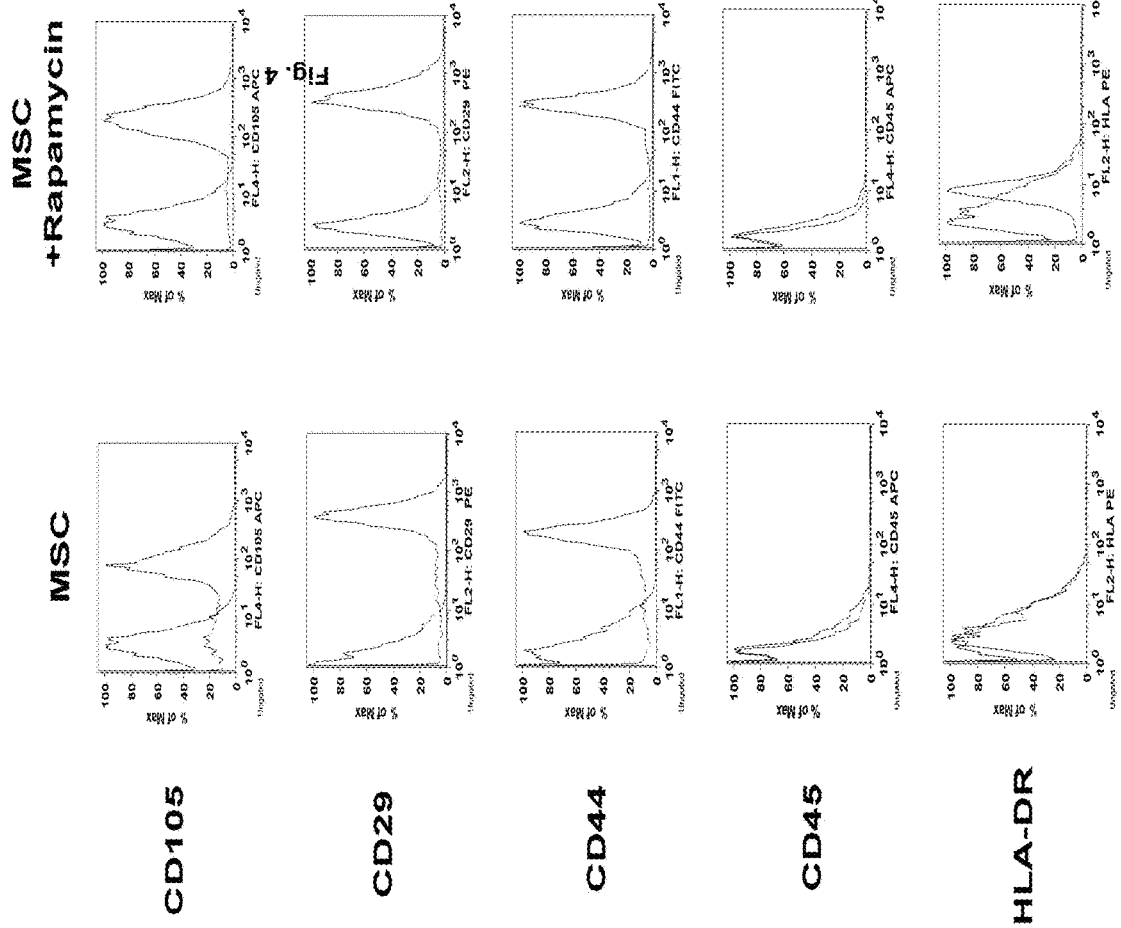
FIG. 4 shows the analysis results of the phenotypes of the mesenchymal stem cells treated with rapamycin and the mesenchymal stem cells not treated with rapamycin.

As a result of the analysis, as shown in FIG. 4, the mesenchymal stem cells in the group treated with rapamycin showed a similar level in the expression of CD105, CD29, and CD44, which are positive markers, like the group without treating it with rapamycin, whereas the expression of CD45 and HLA-DR, which are negative markers, was observed to be both negative.

<Example 5> Analysis of Formation of Autophagic Vacuoles in Rapamycin-Treated Mesenchymal Stem Cells The present inventors have confirmed based on the result in Example 6 below that the rapamycin-treated mesenchymal stem cells showed an increase in the expression of proteins associated with autophagy. In particular, Beclin-1 and LC3, being proteins which increase expression during autophagy, Beclin-1 is known to play an important role in the formation of autophagosome, and LC3 serves as a direct indicator for autophagosome because LC3 is converted from the LC3I form into the LC3II form, out of the two types of LC3, and becomes bound to the membrane of autophagosome upon occurrence of autophagy.

Meanwhile, autophagy has the effects capable of controlling the beneficial or harmful effects of immunity and inflammation, and preventing autoimmunity and inflammatory diseases, and thus the rapamycin-treated mesenchymal stem cells of the present invention, due to their autophagy, can be more effectively used for the immunity and treatment of inflammatory diseases. As such, the present inventors treated the mesenchymal stem cells with 50 μM rapamycin and the degree of formation of autophagic vacuoles was observed under electron microscope.

Figure 5:
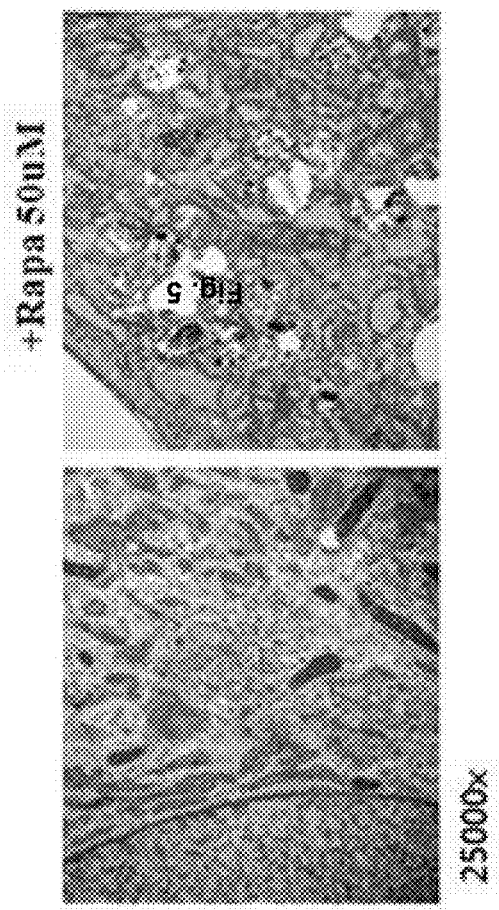
FIG. 5 shows the images observed under a microscope of the phagocytic vacuoles formed in the mesenchymal stem cells derived from human adipose tissues prepared by rapamycin treatment.

As a result of the analysis, as shown in FIG. 5, the number of autophagic vacuoles was shown to increase, and the red arrows in the figure indicate the autophagic vacuoles.

Accordingly, from these results, it was confirmed that the rapamycin-treated mesenchymal stem cells are useful for the treatment of mitochondrial disease.

<Example 6> Analysis of Changes in Expression of Genes Associated with Autophagy in the Rapamycin-Treated Mesenchymal Stem Cells <6-1> Analysis by RT-PCR The adipose tissue-derived mesenchymal stem cells isolated and cultured in Example 1 were treated with 10 ng/mL rapamycin, and 12 hours later, the cells were collected and the total RNA was obtained therefrom. Then, cDNA Synthesis Kit (Roche, Transcriptor First Strand cDNA Synthesis Kit) was prepared based on the RNA. Then, the expression levels of ATG5, LC3A, and LC3B genes, which are autophagy factor markers, were analyzed via real-time PCR using the thus-synthesized cDNA. Each of the primer sequences used for the PCR is shown in the Table 1 below.

TABLE 1

| Primer Name | Primer Sequence (5' to 3') | SEQ ID NO |
|---|---|---|
| ATG5 F-primer | TTTTCACTGTGGTCCCTGGC | 1 |
| ATG5 R-primer | ATCCCCAAAATGAACCGACG | 2 |
| LC3 F-primer | AGACCTTCAAGCAGCGCCG | 3 |
| LC3 R-primer | ACACTGACAATTTCATCCCG | 4 |
| GAPDH F-primer | ACCACAGTCCATGCCATCAC | 5 |
| GAPDH R-primer | TCCACCACCCTGTTGCTGTA | 6 |

As a result of the analysis, as shown in FIG. 6, the group treated with rapamycin showed a significant increase in the expression levels of ATG5, LC3A, and LC3B genes, compared to those of the group not treated with rapamycin.

<6-2> Western Blot Analysis

The present inventors, in furtherance with the result of <6-1>, performed western blot analysis to examine whether mTOR signaling pathway can be controlled by rapamycin, in the rapamycin-treated mesenchymal stem cells. For this purpose, human adipose tissue-derived mesenchymal stem cells were treated with 10 ng/mL rapamycin, and 1 hour later, the cells were lysed and proteins were extracted therefrom. Then, the extracted proteins were subjected to SDS-PAGE electrophoresis, electrically transferred to a nitrocellulose membrane, blocked with 5% skim milk for 1 hour, reacted by attaching primary antibodies to Beclin1, ATG5, ATG7, LC3I, LC3II, Phospho-mTOR, mTOR, Rictor, and Ractor, and then reacted by attaching secondary antibodies thereto, and photosensitized into Kodak X-ray using the Enhanced Chemiluminescence (ECL), and the expression levels of the proteins of these genes were analyzed (FIG. 6c).

As a result of the analysis, as shown in FIG. 6b, it was shown that the mTOR activation (phosphorylation) is inhibited in the mesenchymal stem cell when treated with rapamycin, whereas the expression levels of Beclin1, ATG5, ATG7, LC3I, and LC3II were shown to increase, and in particular, the expression level of ATG7 was shown to be significant.

Accordingly, from these results, the present inventors have confirmed that the mTOR activation and the expression of mTOR signaling factors are inhibited, whereas the expression levels of genes associated with autophagy were increased.

<Example 7> Analysis of Expression of Genes Associated with Cell Migration in Rapamycin-Treated Mesenchymal Stem Cells <7-1> Analysis of Expression of Cell Migration Markers In order to confirm whether adipose tissue-derived mesenchymal stem cell treated with 50 nM rapamycin can migrate into a lesion area due to their cell migration capability, the present inventors analyzed the expression levels of CCR1, CCR2, CCR3, CCR4, CCR7, CCR9, and CXCR4, which are factors associated with the migration of mesenchymal stem cells, via real-time PCR.

As a result of the analysis, as shown in FIG. 7, the rapamycin-treated mesenchymal stem cells apparently showed significant increases in the expression of CCR1 (about a 115-fold), CCR2 (about a 25-fold), CCR3 (about a 70-fold), CCR4 (about a 32-fold), CCR7 (about a 200-fold), CCR9 (about a 150-fold), and CXCR4 (about a 60-fold), compared to those of the group not treated with rapamycin.

<7-2> Analysis of Degree of Cell Migration

For the confirmation of cell migration of the mesenchymal stem cells treated with rapamycin (10 ng/mL), the cells were analyzed using a cell migration kit (Chemicon, Temecula, Calif.). That is, a group with CD4+T cells alone, a group treated with CD4+T cells and rapamycin (10 ng/mL), and a group treated with SDF-1 cells and CD4+T cells were added into the lower chamber, respectively, and the mesenchymal stem cells were added into the upper chamber. Then, for the migration of the adipose tissue-derived mesenchymal stem cells added into the upper chamber into the lower chamber, the cells passed through a polycarbonate membrane were stained and their number was observed by counting.

As a result, it was confirmed that, statistically, the group treated with CD4+T cells and rapamycin (10 ng/mL) had a greater migration compared to the mesenchymal stem cells not treated with anything. However, it was confirmed that the cell migration capability of the rapamycin-treated mesenchymal stem cells was reduced after treatment with bafilomycin, which is an autophagy inhibitor (refer to FIG. 8).

<Example 8> Effect of Rapamycin-Treated Mesenchymal Stem Cells on the Treatment of Osteoarthritis In order to confirm whether the rapamycin-treated mesenchymal stem cells prepared according to the present invention are substantially useful for the treatment of immune disorders, the therapeutic effect was first examined using an animal model induced with osteoarthritis. For the preparation of the animal model induced with osteoarthritis, 5-week old male Wistar mice with a body weight of from 200 g to 250 g (Central Lab. Animal Inc., Korea) were bred at a temperature of from 21° C. to 22° C. with a light-dark cycle at intervals of 12 hours, and provided with sterile water and feeds. Then, for the induction of osteoarthritis, 3 mg of monosodium iodoacetate (Sigma, ST. Louis, Mo.) was injected into the intra-articular of the right knee of each mouse in the amount of 50 µL using a 26.5 G syringe and thereby prepared the animal model induced with osteoarthritis. Then, the mice induced with osteoarthritis were injected intravenously with mesenchymal stem cells ($2 \times 10^6$ cells) and the mesenchymal stem cells treated with rapamycin at a concentration of 100 nM once daily for a total of two times. Seven days thereafter, the degree of pains, which is an indicator for evaluating the effect on the behavior capability of animals induced with osteoarthritis, was measured, and the degree of cartilage destruction was analyzed by India ink method.

As a result of the analysis, as shown in FIG. 9, the group injected with rapamycin-treated mesenchymal stem cells showed a degree of pains being very close to that of normal mice, compared to the group injected with the mesenchymal stem cells, and with respect to the degree of cartilage destruction, the group injected with the rapamycin-treated mesenchymal stem cells also showed a recovery very similar to that of normal mice. Meanwhile, the pictures shown in FIG. 9b represent the areas with cartilage damage, illustrating, from the left, the group of mice induced with osteoarthritis in the first picture, the group treated with MSC after the induction of osteoarthritis in the second picture, and the group treated with the rapamycin-treated MSC after the induction of osteoarthritis in the third picture in this order, and in particular, the group in the third picture was shown to have the least amount of cartilage damage compared with other groups.

<Example 9> Effect of Rapamycin-Treated Mesenchymal Stem Cells on the Treatment of Osteoarthritis Pains and Inflammation For the analysis of the osteoarthritis-induced mice used in <Example 8> regarding the therapeutic effect on osteoarthritis pains and inflammation, the mice were subjected to H&E, Toluidine blue, and Saffranin O stainings.

Figure 10:
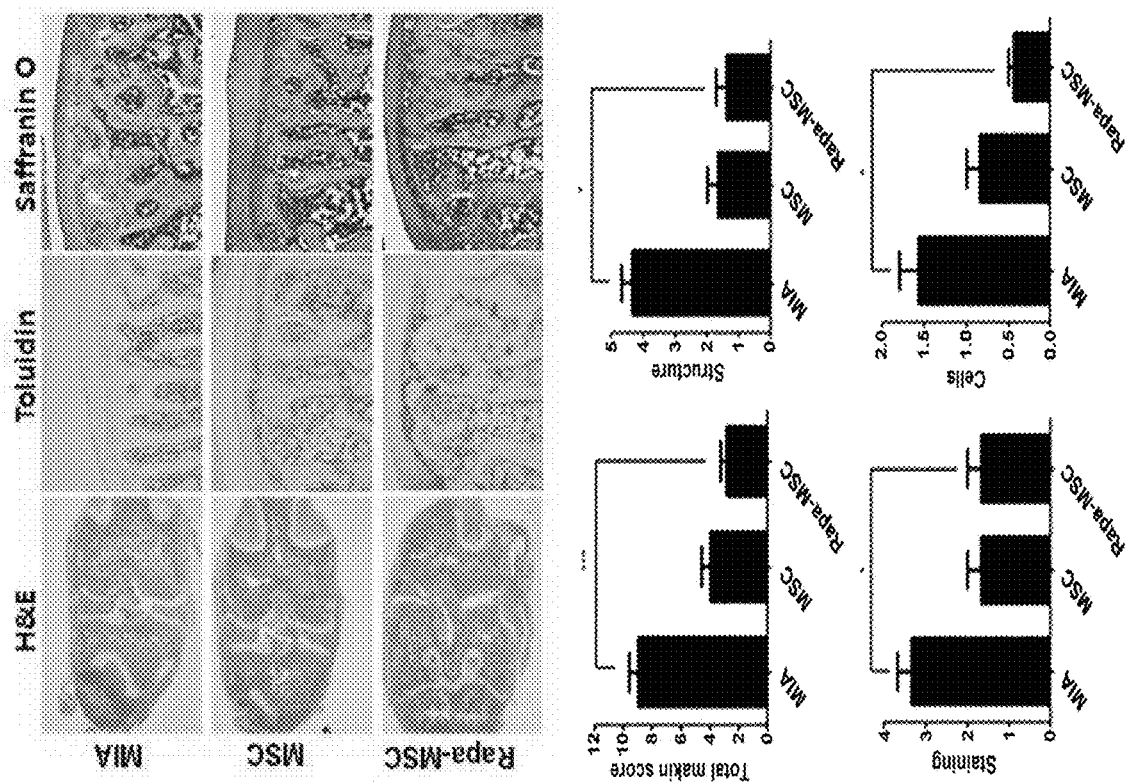
FIG. 10 shows the images of H&E, Toluidine blue staining, and Saffranin O staining performed for the analysis of arthritis and the degree of cartilage damage in an animal induced with osteoarthritis.

As a result of the analysis, as shown in FIG. 10, the group injected with the rapamycin-treated mesenchymal stem cells showed a significant reduction in the degree of invasion of inflammatory cells or cartilage destruction, compared to the group injected with the mesenchymal stem cells (FIG. 10).

<Example 10> Effect of Rapamycin-Treated Mesenchymal Stem Cells on the Treatment of Inflammatory Bowel Disease For the preparation of a mouse model with inflammatory bowel disease, C57BL/6 (H-2 kb) mice were used as experimental animals, and the mice were supplied with 3.5% dextran sulfate sodium (DSS) and water for a week to prepare an animal model induced with inflammatory bowel disease. Then, the animal model induced with inflammatory bowel disease was intravenously was respectively injected with the adipose tissue-derived mesenchymal stem cells ($2\times10^6$ cells) and the adipose tissue-derived mesenchymal stem cells treated with rapamycin ($2\times10^6$ cells), once a week for a total of two times, and the symptoms (body weight, length of large intestine, and disease activity index (DAI)) were confirmed.

As a result of the analysis, as shown in FIG. 11, the group injected with the rapamycin-treated, adipose tissue-derived mesenchymal stem cells showed a more effective recovery of body weight, which was reduced by inflammatory bowel disease, compared to the group treated with the adipose tissue-derived mesenchymal stem cells alone (FIG. 11a), and also the activity of the disease was significantly reduced (FIG. 11b). Additionally, the thickness and the length of the large intestine were shown to have been recovered, and the shortened phenomenon of the length of the intestine was confirmed to have been recovered to be similar to that of normal animals (FIG. 11c).

<Example 11> Effect of Rapamycin-Treated Mesenchymal Stem Cells on the Treatment of Inflammatory Bowel Disease The present inventors have confirmed the disease-controlling effect of rapamycin-treated mesenchymal stem cells in a mouse model with inflammatory bowel disease used in <Example 10> via H&E staining of the tissues of the animal model.

Figure 12A:
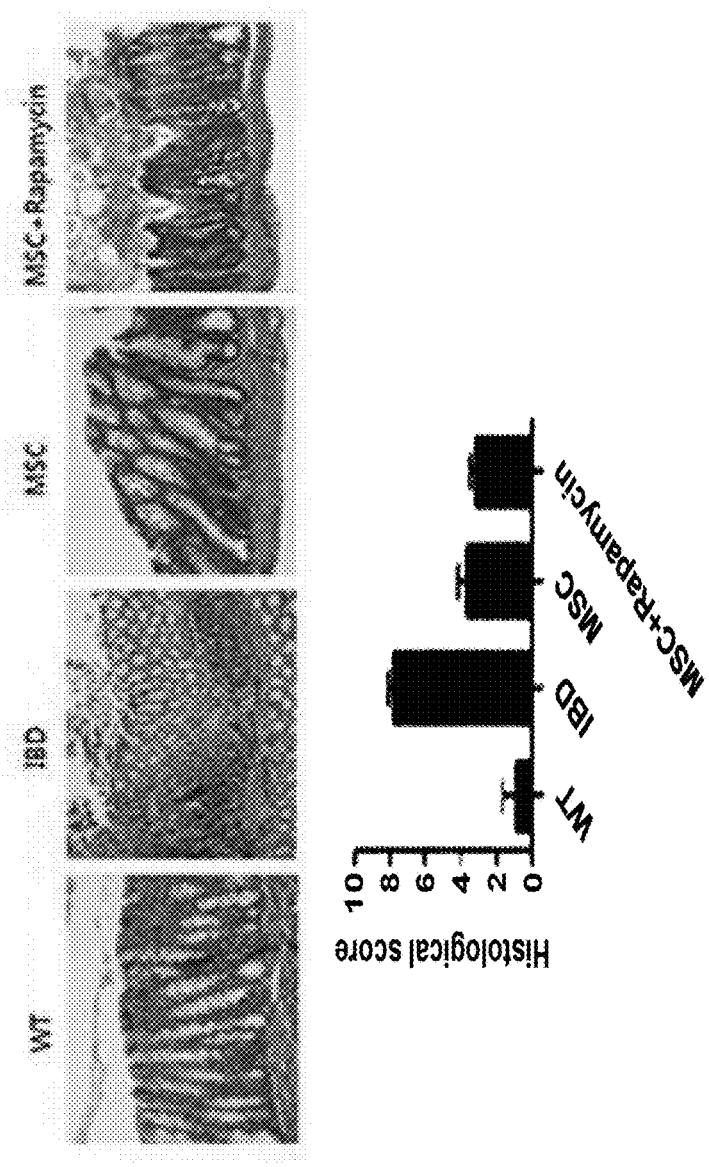
FIGS. 12A-12B show the result of a therapeutic effect of rapamycin-treated mesenchymal stem cells in a mouse model with inflammatory bowel disease confirmed by H&E staining and IHC staining in tissues.
Figure 12B:
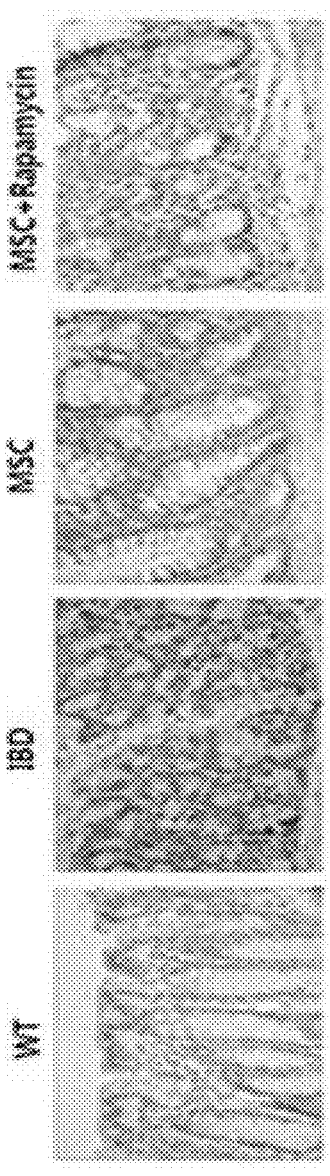

As a result, it was observed that the model injected with the rapamycin-treated mesenchymal stem cells showed a decrease in invasion of inflammatory cells in the intestine (FIG. 12a). Additionally, as a result of IHC staining of TNF-α, an inflammatory cytokine, in the intestine, the model injected with the rapamycin-treated mesenchymal stem cells were shown to have a significantly reduced amount of TNF-α compared to the group induced with the disease (FIG. 12b).

<Example 12> Effect of Rapamycin-Treated Mesenchymal Stem Cells on the Treatment of Arthritis In order to confirm whether the rapamycin-treated mesenchymal stem cells have a therapeutic effect on arthritis, the present inventors have conducted experiments as follows. First, for the preparation of a mouse model with an autoimmune arthritis, an IL-1Ra knockout mouse, in which IL-1 receptor gene was knocked out, was prepared according to the method disclosed by the Y. Iwakura research team, and this is a method to naturally induce an autoimmune arthritis disease by allowing the IL-1 receptor antagonist (IL-1Ra) to directly act on IL-1 receptors, thereby preventing IL-1α and IL-1 from action on receptor. The arthritis-induced mice were injected with the rapamycin-treated mesenchymal stem cells, prepared in the present invention, and the rapamycin-treated mesenchymal stem cells ($2\times10^6$ cells) were intravenously injected into the mice once a week for a total of three times, and the serum was isolated from these mice one week thereafter, and the amount of IgG, IgG1, and IgG2a present in the serum were analyzed. In particular, for the control group, those for which the amount of the above immunoglobulins for the serum of the arthritis-induced mouse and the serum of the arthritis-induced, adipose tissue-derived mouse was measured were used.

Figures 13A, 13B:
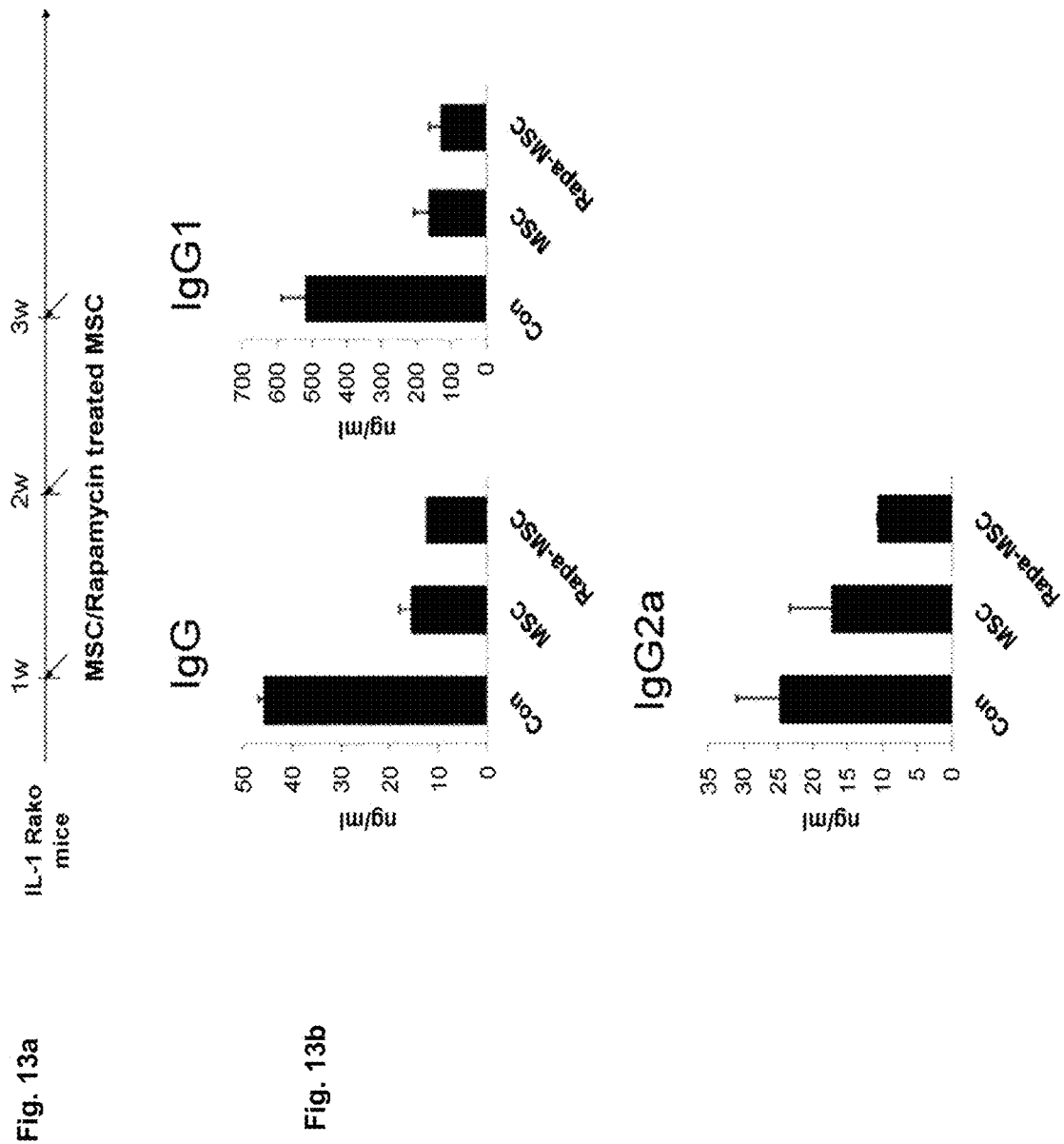
FIGS. 13A-13B show the result of concentration of IgG, IgG1, and IgG2a in the serum of a mouse model with arthritis observed as a therapeutic effect by rapamycin-treated mesenchymal stem cells.

As a result of the analysis, the group of mice injected with the rapamycin-treated mesenchymal stem cells showed an improvement in the symptoms of arthritis compared to the group treated with mesenchymal stem cells alone, and the production of IgG1 of Th2 type and IgG2a of Th1 type, which act on immune responses, were both significantly reduced (FIG. 13).

Accordingly, from these results, the present inventors have confirmed that the rapamycin-treated mesenchymal stem cells have the immune response controlling activity, and thus they can be effectively used as a therapeutic agent especially for the treatment of autoimmune disorders.

<Example 13> Effect of Rapamycin-Treated Mesenchymal Stem Cells on the Treatment of Arthritis In order to confirm the therapeutic effect of the rapamycin-treated mesenchymal stem cells and that of the general mesenchymal stem cells, the present inventors have confirmed their therapeutic effects by administering them to animal models with rheumatoid arthritis through the induction of the activity of self-antigens. For the preparation of animals with arthritis, each of the DBA/1J mouse was injected at the tail base with 100 µg of type II collagen (CII) at a volume of 50 µL, in which CII and CFA (adjuvant) were mixed at a 1:1 ratio, and two weeks thereafter, the mixed solution, in which CII and IFA were mixed at a 1:1 ratio, and secondly injected in an amount of 100 μg/50 μL. The mice were induced with arthritis, and one week thereafter, the untreated mesenchymal stem cells ($1 \times 10^6$ cells to $5 \times 10^7$ cells/kg of body weight) or the rapamycin-treated mesenchymal stem cells ($1 \times 10^6$ cells to $5 \times 10^7$ cells/kg of body weight) were injected intravenously once a week for a total of three times, and the arthritis was evaluated. One week after inducing the mice with arthritis, the untreated mesenchymal stem cells ($1 \times 10^6$ cells) or the rapamycin-treated mesenchymal stem cells ($1 \times 10^6$ cells) were injected intravenously once a week for a total of three times, and the arthritis was evaluated. For the measurement of arthritis index, three observers who were not aware of the details of the experiment conducted evaluations on the severity of inflammation of arthritis three times a week and the observation was continued until day 29. In particular, the evaluation of arthritis was conducted as follows. Based on the mean arthritis index by Rossoliniec et al., the scores for each mouse rendered on the remaining three legs other than the leg, which was injected with the CII/CFA at the secondary injection, according to the following guideline were combined, divided by 3 to obtain a mean value, and again another mean value, which was obtained by combining the scores obtained by three observers in each animal model and divided thereafter, were used. The criteria and the scores for the evaluation of arthritis are as follows.

0 point: no edema or swelling
1 point: slight edema and redness restricted to leg and ankle joint
2 points: slight edema and redness from ankle joint to metatarsal
3 points: moderate edema and redness from ankle joint to metatarsal
4 points: edema and redness from ankle to the entire leg In particular, the highest arthritis index for each mouse is 4 points, and thus the highest disease index for each mouse is 16.

Figure 14:
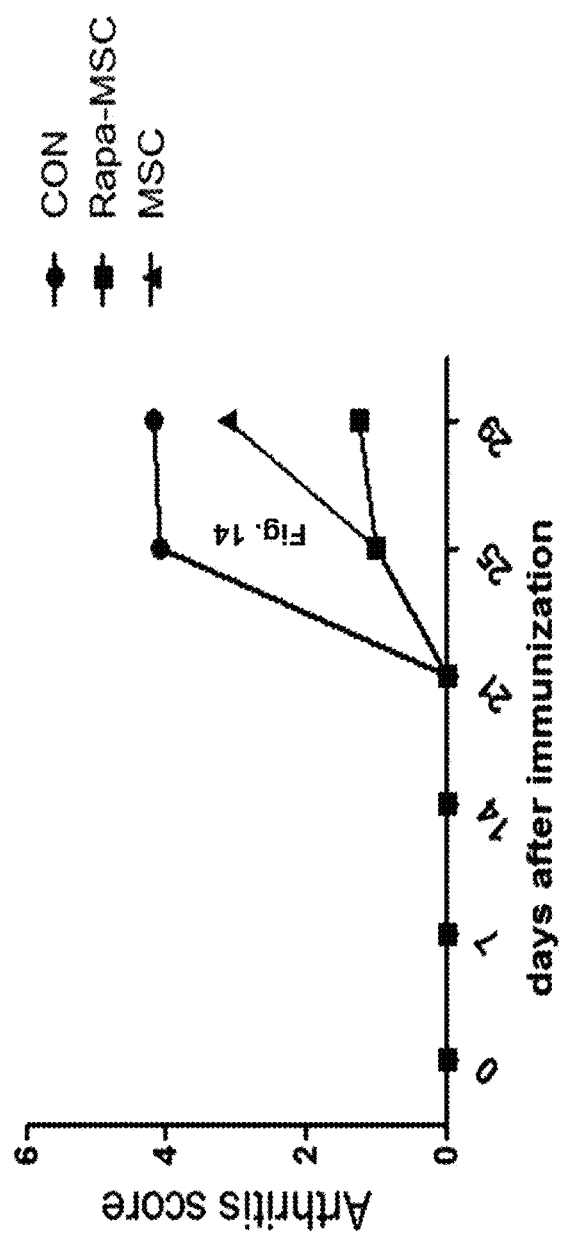
FIG. 14 shows the graph illustrating the change in arthritis index for each of the animal model induced with osteoarthritis, in a group treated with mesenchymal stem cells alone (MSC) and in a group treated with rapamycin-treated mesenchymal stem cells (Rapa-MSC), according to an exemplary embodiment of the present invention.

As a result of the analysis, as shown in FIG. 14, the group of mice injected with the rapamycin-treated mesenchymal stem cells was more significantly inhibited of arthritis compared to the group injected with the mesenchymal stem cells.

<Example 14> Effect of Rapamycin-Treated Mesenchymal Stem Cells on the Treatment of Transplant Rejection Disease In order to confirm whether the rapamycin-treated mesenchymal stem cells also have a therapeutic effect on transplant rejection disease, the present inventors have conducted experiments as follows.

<14-1> Analysis of Therapeutic Effect on Transplant Rejection Disease

First, for the preparation of an animal model with transplant rejection disease, the recipient mouse, Balb/c (H-2k/d), was subjected to total body irradiation (TBI) at a dose of 800 cGy, and hematopoietic stem cells and spleen cells were isolated from the femur and tibia of the donor mouse C57BL/6 (H-2k/$^b$), and the hematopoietic stem cells ($5 \times 10^6$ cells) and the spleen cells ($1 \times 10^6$ cells) were transplanted into the recipient mouse, Balb/c (H-2k/$^d$).

After the transplant, the untreated mesenchymal stem cells ($1 \times 10^6$ cells) or the rapamycin-treated mesenchymal stem cells ($1 \times 10^6$ cells) were administered intraperitoneally, and the evaluation on their efficacy was conducted.

Figure 15A:
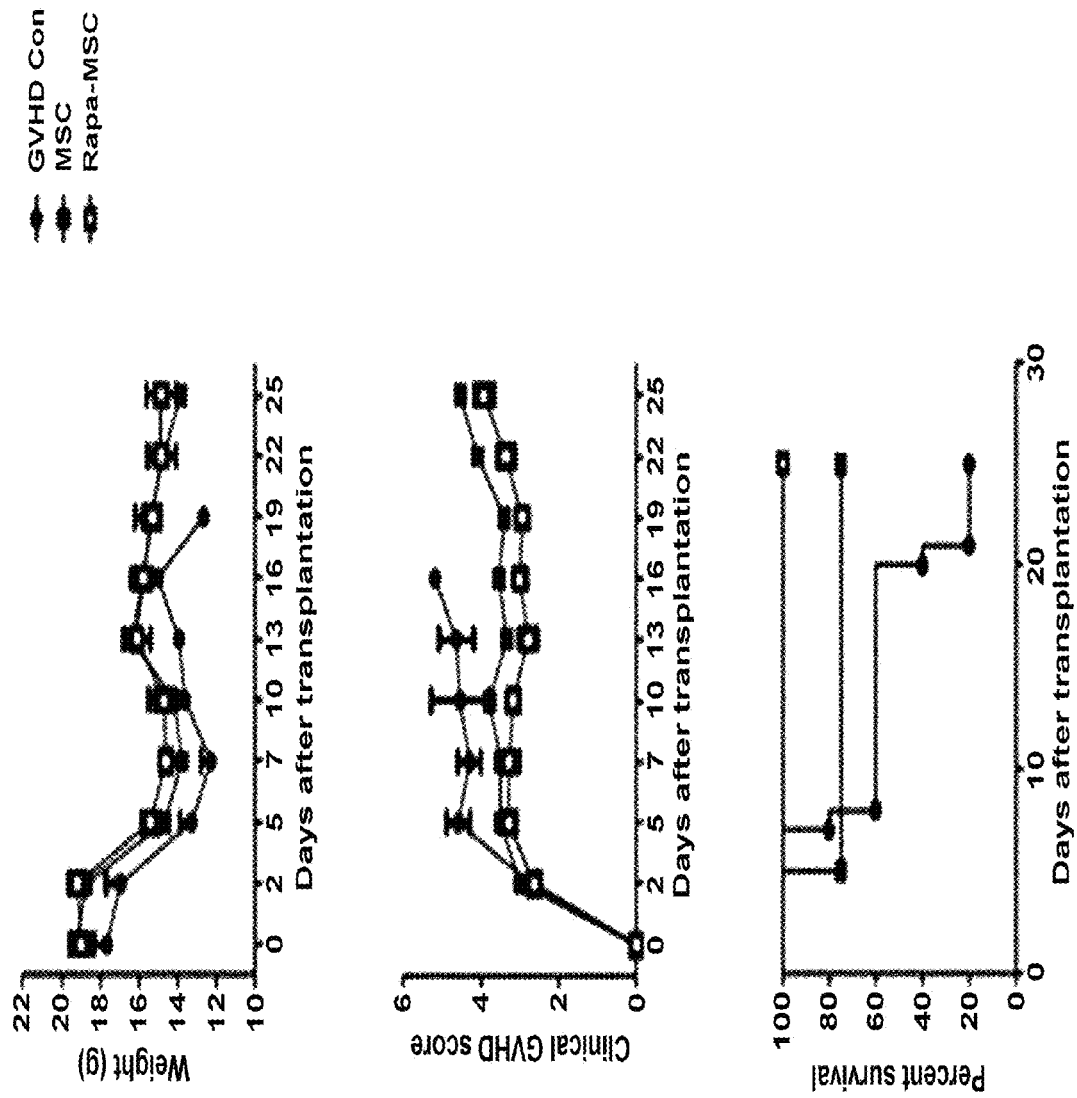
FIGS. 15a to 15c show the result of therapeutic effect of rapamycin-treated mesenchymal stem cells after injection into an animal model for a transplant rejection disease.

As a result of the analysis, upon observation of the body weight, degree of disease, and degree of survival, it was confirmed that the group of mice injected with the rapamycin-treated mesenchymal stem cells were shown to have an improvement in the degree of disease of the mouse with transplant rejection disease compared to the group injected with the mesenchymal stem cells, and the degree of survival was also maintained for 30 days (FIG. 15a).

<14-2> Analysis of Invasion of Inflammatory Cells in a Mouse Model Injected with Rapamycin-Treated Mesenchymal Stem Cells First, the model mouse with transplant rejection disease was injected with the rapamycin-treated mesenchymal stem cells prepared in the present invention. One week after the transplant, the skin and the organ (the liver) of the mouse were collected, fixed with 10% neutral buffered formalin, embedded in paraffin, and tissue slices were prepared and attached to slides. Before performing the basic staining, the tissue slices went through deparaffinization process using xylene, and dipped into ethanol from high concentration to low concentration. The staining process was performed using hematoxylin and eosin.

Figure 15B:
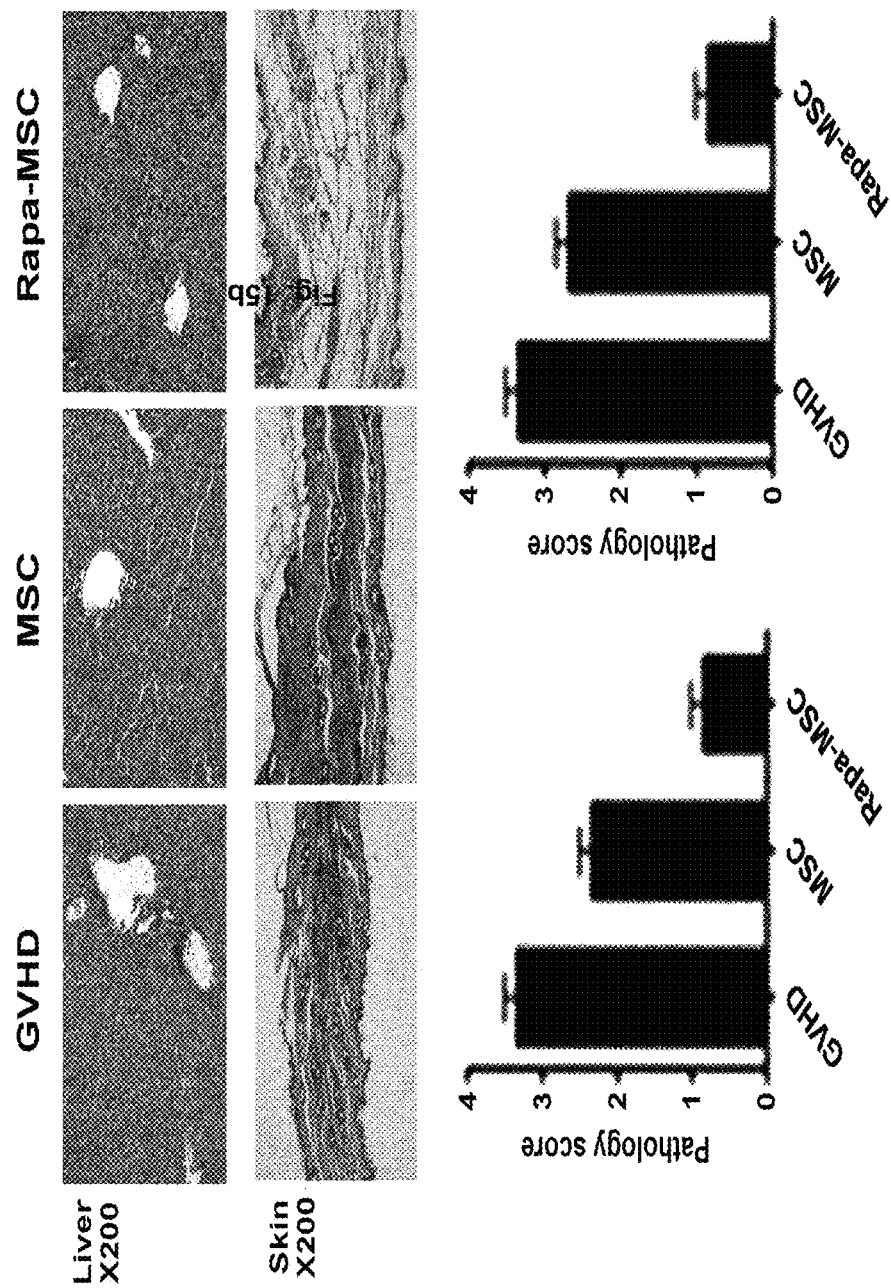

As a result of the analysis, the group of mice injected with the rapamycin-treated mesenchymal stem cells were shown to have a significantly reduced invasion of the inflammatory cells compared to the group injected with the mesenchymal stem cells alone (FIG. 15b).

<14-3> Analysis of Cytokines and T Cells in Spleen Cells in a Mouse Model Injected with Rapamycin-Treated Mesenchymal Stem Cells First, spleens were collected from a model mouse with transplant rejection disease. Cytokines (IFN-γ, IL-17, IL-4, and Foxp) from the collected spleens were stained via immunohistochemical staining and analyzed under optical microscope, and the T cell subset in the spleen cells of each mouse was analyzed.

Figure 15C:
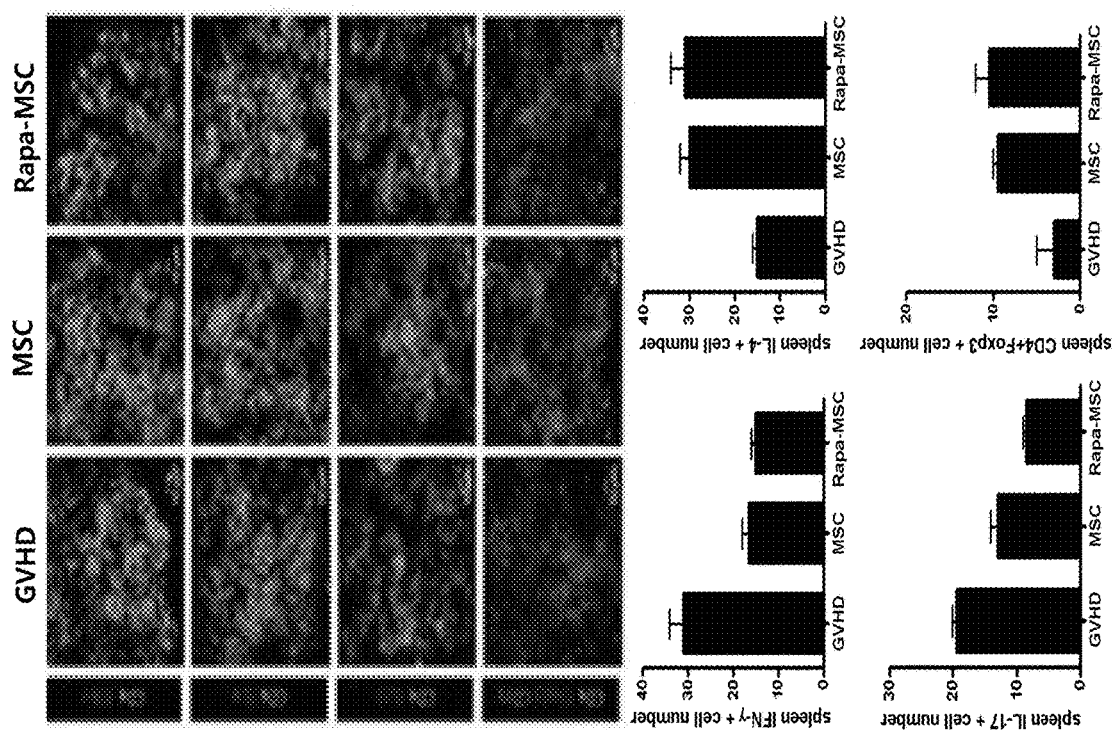

As a result of the analysis, the group of mice injected with the rapamycin-treated mesenchymal stem cells were shown to have a significant decrease in Th1 (IFN-γ) cells and Th17 (IL-17) cells, which are etiological cells, while having a significant increase in Th2(IL-4) cells and Treg(Foxp3+) cells (FIG. 15c).

Accordingly, from these results, the present inventors have confirmed that the rapamycin-treated mesenchymal stem cells have the immune response controlling activity, and thus they can be effectively used as a therapeutic agent especially for the treatment of autoimmune disorders.

<Example 15> Induction Analysis of the Activity of Immunomodulatory T Lymphocytes when Rapamycin-Treated Mesenchymal Stem Cells are Co-Cultured with Etiological T Lymphocytes of an Animal Model with Lupus The present inventors have examined the immunomodulatory activity of the rapamycin-treated, adipose tissue-derived mesenchymal stem cells on the cells of an animal model with lupus. A mouse with Roquin gene mutation is a mouse model with autoimmune disorder similar to that of lupus due to overexpression of self-antibody caused by the induction of activity of Th cells and the increase of Germinal center response, the cells were isolated from the Roquin mouse, which is an animal model with lupus, and co-cultured with mesenchymal stem cells in a 1:10 ratio for 3 days, and the activity of the immunomodulatory T cells (Foxp3+Treg) was analyzed via flow cytometry analysis.

Figure 16:
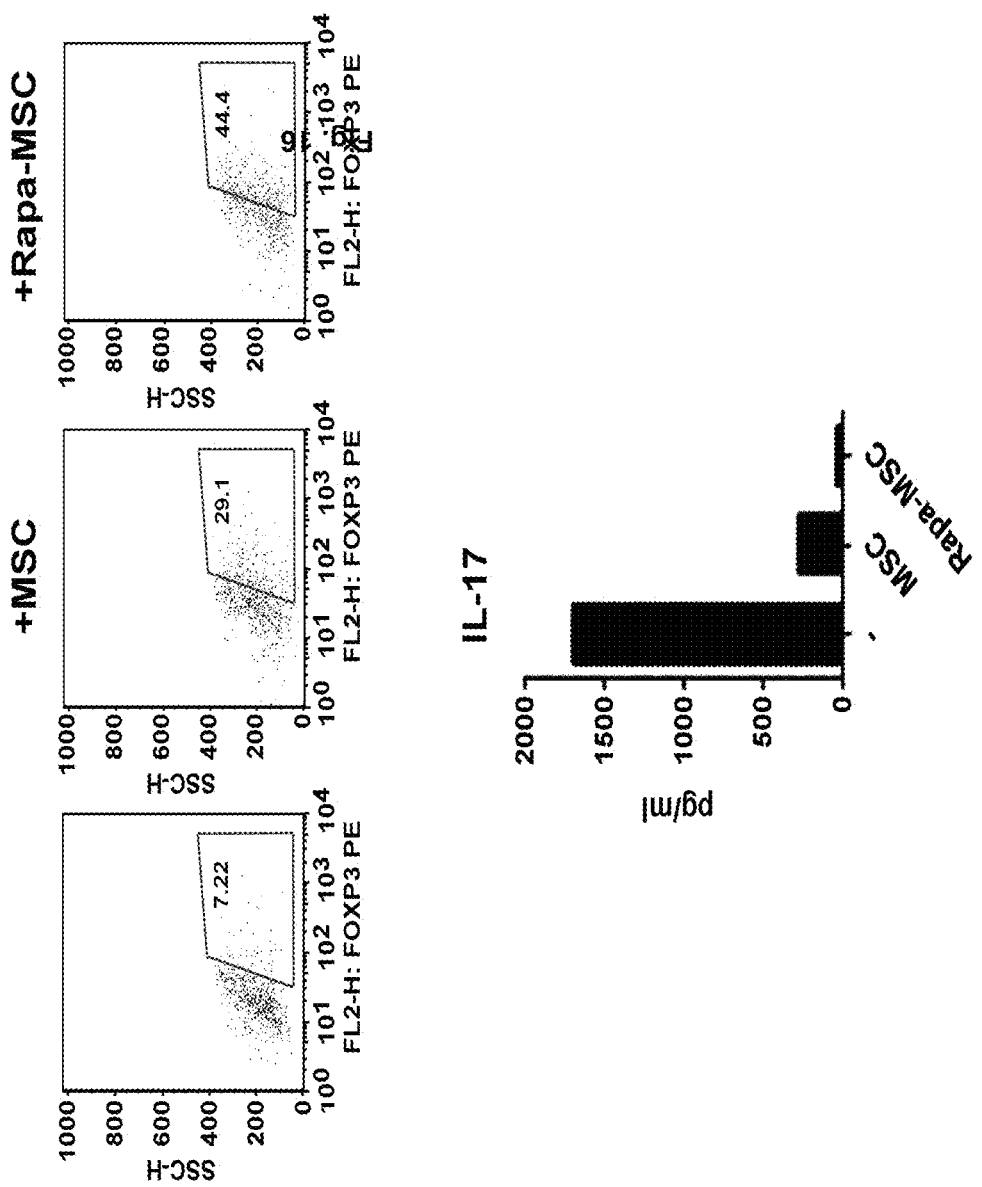
FIG. 16 shows the confirmed result of immunomodulating capability of rapamycin-treated mesenchymal stem cells derived from adipose tissue on an animal model with lupus.

As a result of the analysis, as shown in FIG. 16, the group of mice treated with rapamycin was shown to have a significant decrease in the amount of IL-17 in the culture broth, and the activity of the immunomodulatory T cells was further increased.

Accordingly, from these results, the present inventors have confirmed that the mesenchymal stem cells, by rapamycin-treatment, can be effectively used as a therapeutic agent especially for the treatment of autoimmune disorders.

<Example 16> Induction Analysis of the Activity of Immunomodulatory T Lymphocytes when Rapamycin-Treated Mesenchymal Stem Cells are Co-Cultured with Etiological T Lymphocytes of a Patient with Rheumatoid Arthritis The present inventors have examined the immunomodulatory activity of the rapamycin-treated mesenchymal stem cells derived from a rheumatoid patient. The mouse CD4+T cells ($1 \times 10^5$ cells) and the mesenchymal stem cells ($1 \times 10^4$ cells) derived from the rheumatoid patient were co-cultured in a 1:10 ratio in a 96-well plate at 37° C., and the activity of the immunomodulatory T cells (Foxp3+Treg) was analyzed via flow cytometry analysis.

Figure 17:
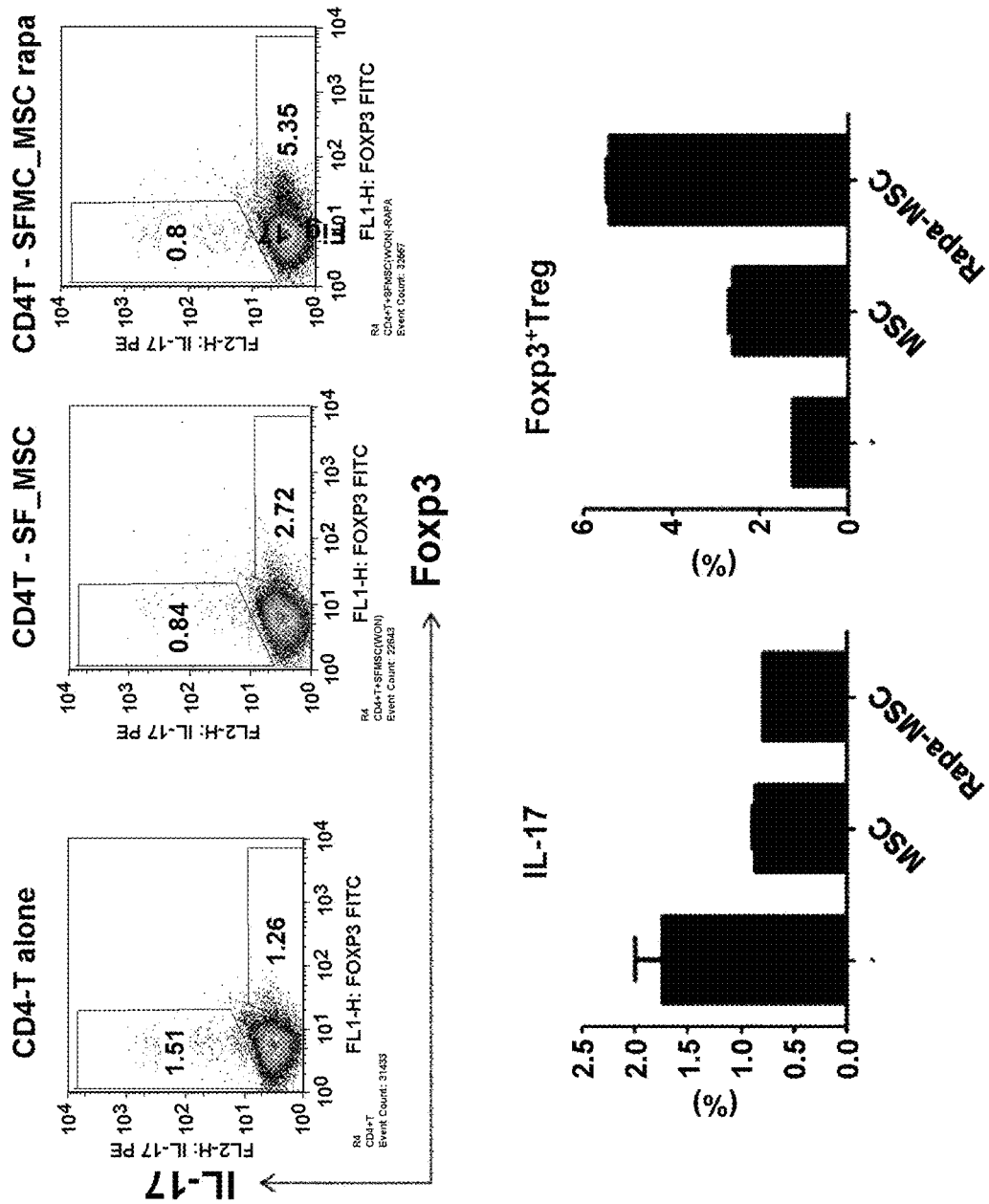
FIG. 17 shows the result of Th17 and Treg cell regulating effect of rapamycin and mesenchymal stem cells of the present invention confirmed by a fluorescence-activating cell sorting (FACS), according to an exemplary embodiment of the present invention.

As a result of the analysis, as shown in FIG. 17, the group of mice treated with rapamycin was shown to have a significant decrease in the amount of IL-17 in the culture broth, and the activity of the immunomodulatory T cells was further increased.

Accordingly, from these results, the present inventors have confirmed that the mesenchymal stem cells, by rapamycin-treatment, can be effectively used as a cell therapeutic agent especially for the treatment of autoimmune disorders Those of ordinary skill in the art will recognize that the present invention may be embodied in other specific forms without departing from its spirit or essential characteristics. The described embodiments are to be considered in all respects as only illustrative and not restrictive. The scope of the present invention is, therefore, indicated by the appended claims rather than by the foregoing description. All changes which come within the meaning and range of equivalency of the claims are to be embraced within the scope of the present invention.

The present invention was performed being sponsored by the National Research Development Business Program described below.

1. Project No.: 2012M3A9C6049783
2. Name of Research Business: Biomedical Technology Development Business Cell Regeneration Technology Development Business
3. Name of Research Project: Development of Therapeutic Technology for Treating Autoimmune disorders using Inflammasome controlling factor-specific Mesenchymal Stem Cells
4. Agency in charge: Industry-Academic Cooperation Foundation, the Catholic University of Korea
5. Government Department: Ministry of Education and Science Technology (MEST)
6. National R&D Management Agency: National Research Foundation of Korea (NRF)
7. Research Period: Oct. 1, 2012 to Sep. 30, 2013

The invention claimed is:

1. A method of treating inflammatory bowel disease or systemic lupus erythematosus, the method comprising administering to a subject in need thereof a rapamycin-treated mesenchymal stem cell having immunomodulatory activity in an amount of $1\times10^6$ to $5\times10^7$ cells per kg of body weight of a subject, wherein the rapamycin-treated mesenchymal stem cell expresses cell surface factors consisting of CCR1, CCR2, CCR3, CCR4, CCR7, CCR9, and CXCR4, and wherein the rapamycin-treated mesenchymal stem cell is prepared comprising the steps of:

i) obtaining the mesenchymal stem cell in an amount of $5\times10^5$ cells isolated from peripheral blood or adipose tissue, ii) treating the obtained cells with rapamycin at a concentration of from 10 nM to 100 nM, and iii) culturing the treated cells at from 28° C. to 42° C. for 18 hours to 27 hours.

2. The method of claim 1, wherein the disease is inflammatory bowel disease.

3. The method of claim 1, wherein the disease is systemic lupus erythematosus.

4. The method of claim 1, wherein the disease is inflammatory bowel disease and systemic lupus erythematosus.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: ATG5 F-primer

<400> SEQUENCE: 1
ttttcactgt ggtccctggc                                              20

<210> SEQ ID NO 2
<211> LENGTH: 20
<212> TYPE: DNA
<213> ORGANISM: Artificial Sequence
<220> FEATURE:
<223> OTHER INFORMATION: ATG5 R-primer

<400> SEQUENCE: 2
atccccaaaa tgaaccgacg                                              20

<210> SEQ ID NO 3
<211> LENGTH: 19
<212> TYPE: DNA
<213> ORGANISM: Artificial Sequence
<220> FEATURE:
<223> OTHER INFORMATION: LC3 F-primer

<400> SEQUENCE: 3
agaccttcaa gcagcgccg                                               19

<210> SEQ ID NO 4
```

```
<211> LENGTH: 20
<212> TYPE: DNA
<213> ORGANISM: Artificial Sequence
<220> FEATURE:
<223> OTHER INFORMATION: LC3 R-primer

<400> SEQUENCE: 4
acactgacaa tttcatcccg                                               20

<210> SEQ ID NO 5
<211> LENGTH: 20
<212> TYPE: DNA
<213> ORGANISM: Artificial Sequence
<220> FEATURE:
<223> OTHER INFORMATION: GAPDH F-primer

<400> SEQUENCE: 5
accacagtcc atgccatcac                                               20

<210> SEQ ID NO 6
<211> LENGTH: 20
<212> TYPE: DNA
<213> ORGANISM: Artificial Sequence
<220> FEATURE:
<223> OTHER INFORMATION: GAPDH R-primer

<400> SEQUENCE: 6
tccaccaccc tgttgctgta                                               20
```